US009603509B2

(12) United States Patent
Ando

(10) Patent No.: US 9,603,509 B2
(45) Date of Patent: Mar. 28, 2017

(54) ENDOSCOPE CHANNEL SWITCHING APPARATUS

(71) Applicant: OLYMPUS CORPORATION, Shibuya-ku, Tokyo (JP)

(72) Inventor: Atsushi Ando, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 423 days.

(21) Appl. No.: 14/295,086

(22) Filed: Jun. 3, 2014

(65) Prior Publication Data

US 2014/0288372 A1 Sep. 25, 2014

Related U.S. Application Data

(63) Continuation of application No. PCT/JP2013/062824, filed on May 7, 2013.

(30) Foreign Application Priority Data

May 23, 2012 (JP) ................................. 2012-117718

(51) Int. Cl.
| | | |
|---|---|---|
| *A61B 1/12* | (2006.01) | |
| *A61B 1/015* | (2006.01) | |
| *G02B 23/24* | (2006.01) | |
| *A61B 1/00* | (2006.01) | |
| *F04B 9/14* | (2006.01) | |

(52) U.S. Cl.
CPC .......... *A61B 1/015* (2013.01); *A61B 1/00068* (2013.01); *A61B 1/126* (2013.01); *F04B 9/14* (2013.01); *G02B 23/2476* (2013.01)

(58) Field of Classification Search
CPC ............................ A61B 1/00068; A61B 1/015

USPC .................................................. 600/153–159
See application file for complete search history.

(56) References Cited

U.S. PATENT DOCUMENTS

| | | | | | |
|---|---|---|---|---|---|
| 4,361,138 | A | * | 11/1982 | Kinoshita ........... | A61B 1/00068 600/159 |
| 5,840,016 | A | * | 11/1998 | Kitano ..................... | A61B 1/12 251/335.2 |
| 6,346,075 | B1 | * | 2/2002 | Arai ....................... | A61B 1/015 600/159 |
| 9,307,890 | B2 | * | 4/2016 | Ouchi ................ | A61B 1/00068 |
| 2008/0183037 | A1 | * | 7/2008 | Ichikawa ........... | A61B 1/00068 600/104 |

(Continued)

FOREIGN PATENT DOCUMENTS

| | | |
|---|---|---|
| JP | 09122069 A | 5/1997 |
| JP | 2010082394 A | 4/2010 |

OTHER PUBLICATIONS

Japanese Office Action (and English translation thereof) dated Dec. 15, 2015, issued in counterpart Japanese Application No. 2012-117718.

(Continued)

*Primary Examiner* — Matthew J Kasztejna
(74) *Attorney, Agent, or Firm* — Holtz, Holtz & Volek PC

(57) ABSTRACT

A check valve unit includes a low-strength part and a high-strength part which are provided in the side of a head part of the check valve unit moving and have strength levels which differ from each other. The low-strength part and high-strength part are arranged alternately in circumferential directions of the check valve unit.

4 Claims, 16 Drawing Sheets

(56) References Cited

U.S. PATENT DOCUMENTS

| | | | |
|---|---|---|---|
| 2012/0088975 A1* | 4/2012 | Morimoto | A61B 1/015 600/159 |
| 2015/0011831 A1* | 1/2015 | Ouchi | A61B 1/00068 600/159 |
| 2015/0257634 A1* | 9/2015 | Nakade | A61B 1/00068 600/159 |

OTHER PUBLICATIONS

International Preliminary Report on Patentability (IPRP) including Written Opinion dated Nov. 25, 2014, issued in parent International Application No. PCT/JP2013/062824.
International Search Report (ISR) dated Jun. 11, 2013 issued in International Application No. PCT/JP2013/062824.
Chinese Office Action (and English translation thereof) dated Aug. 3, 2015, issued in counterpart Chinese Application No. 201380004241.7.

* cited by examiner

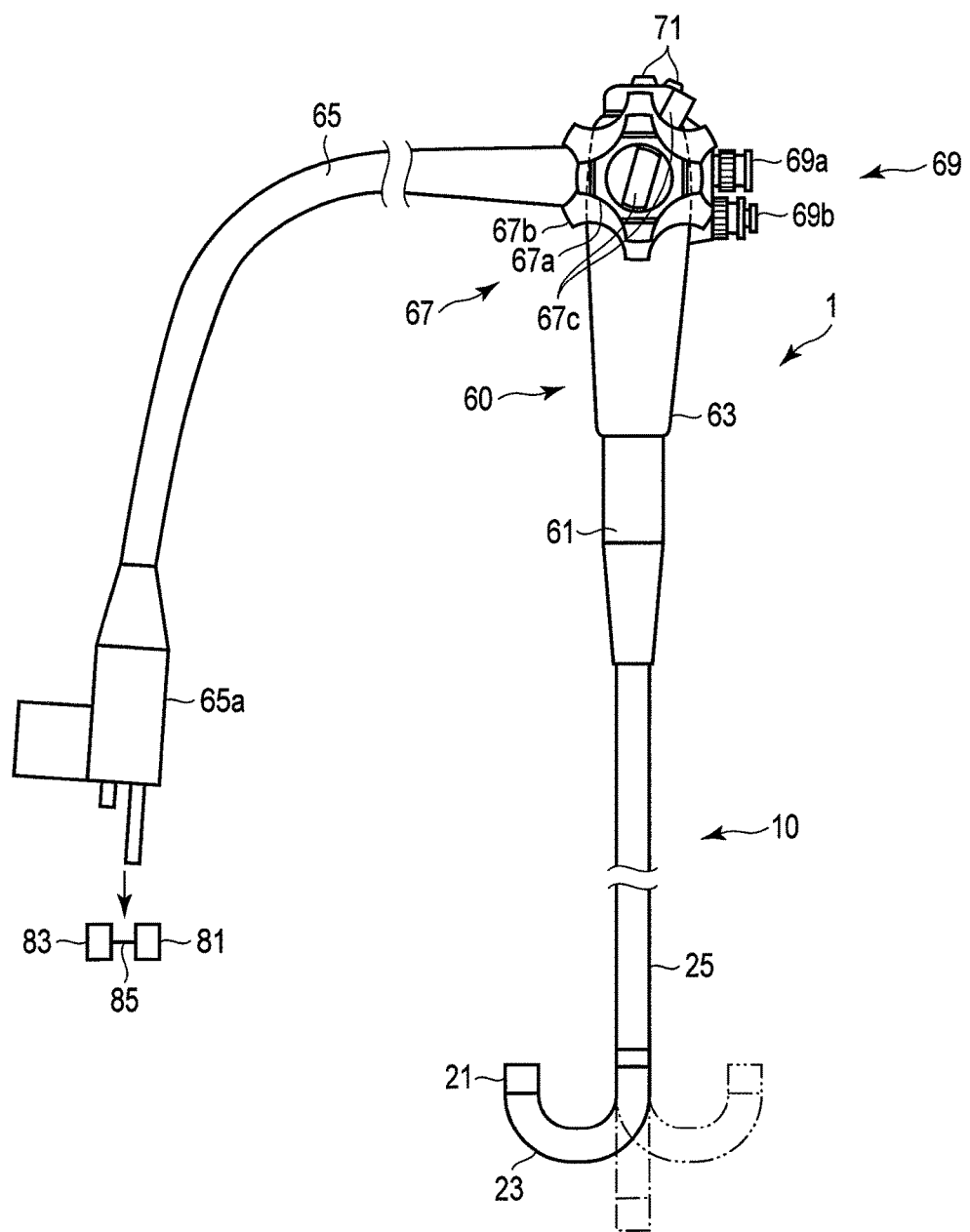
F I G. 1

Step 2

Step 1

Step 2

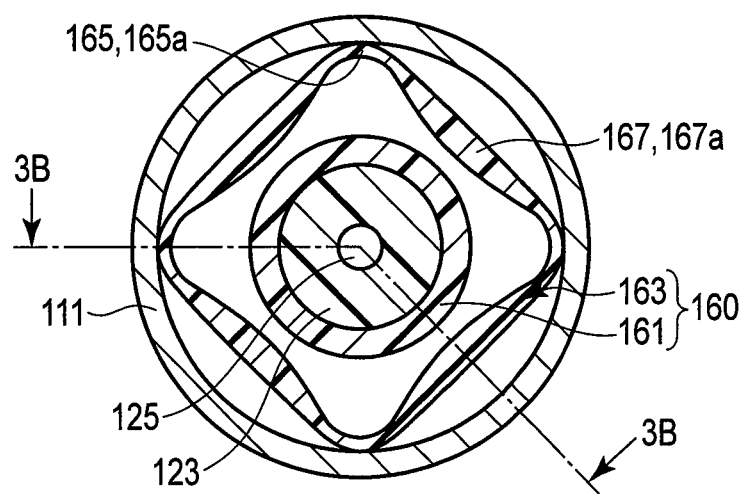
F I G. 3C

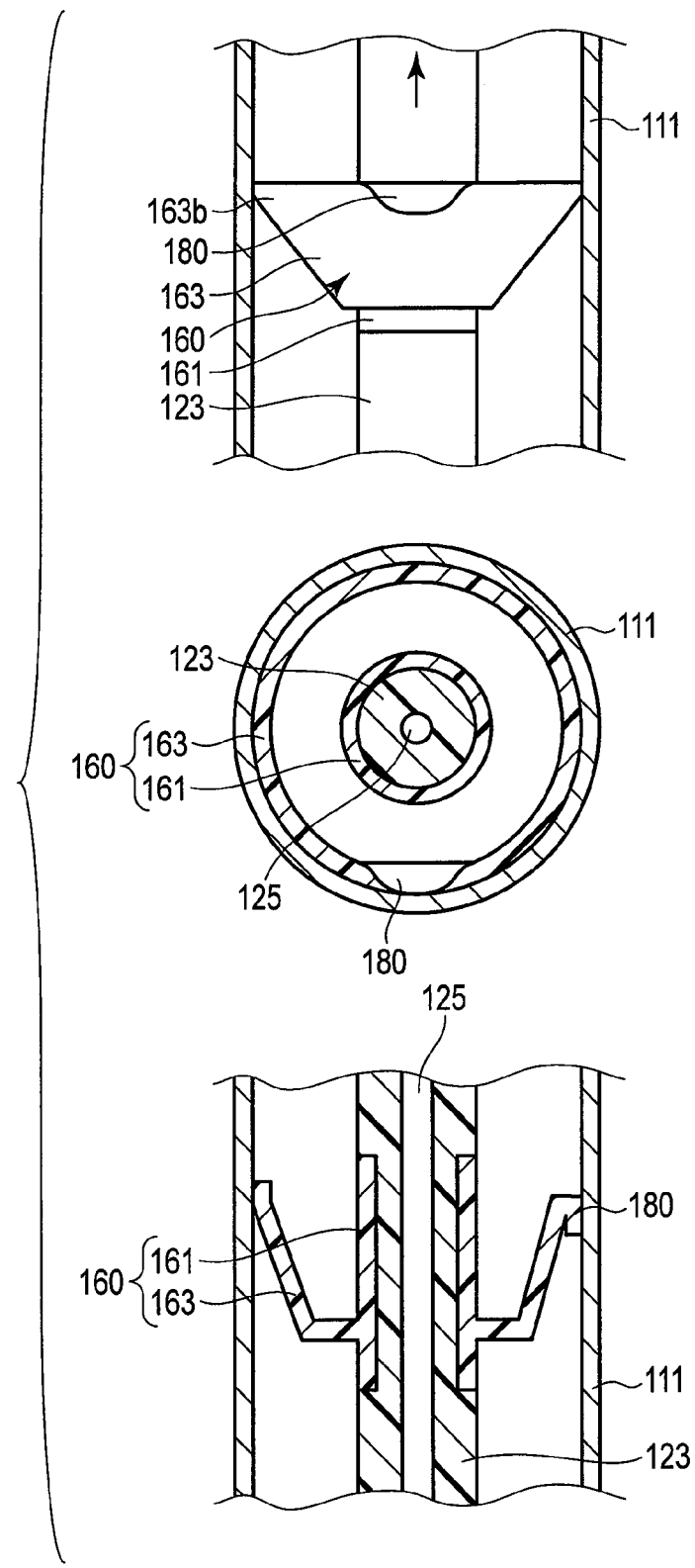
F I G. 4B

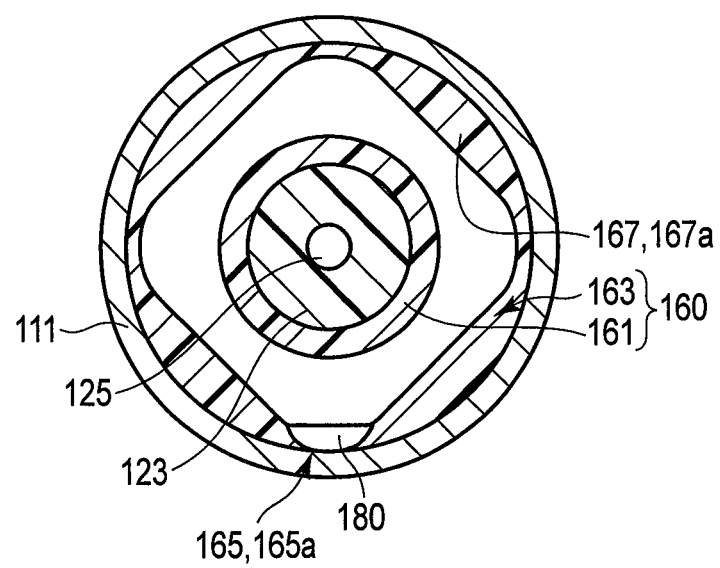
F I G. 4D

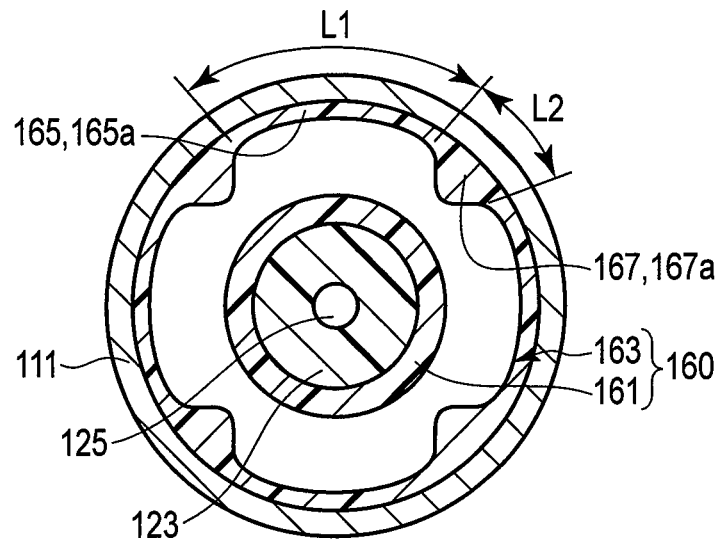
F I G. 5A
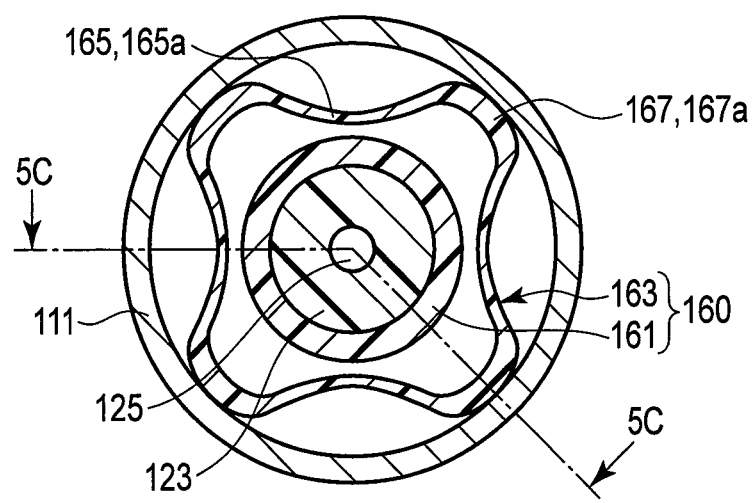
F I G. 5B

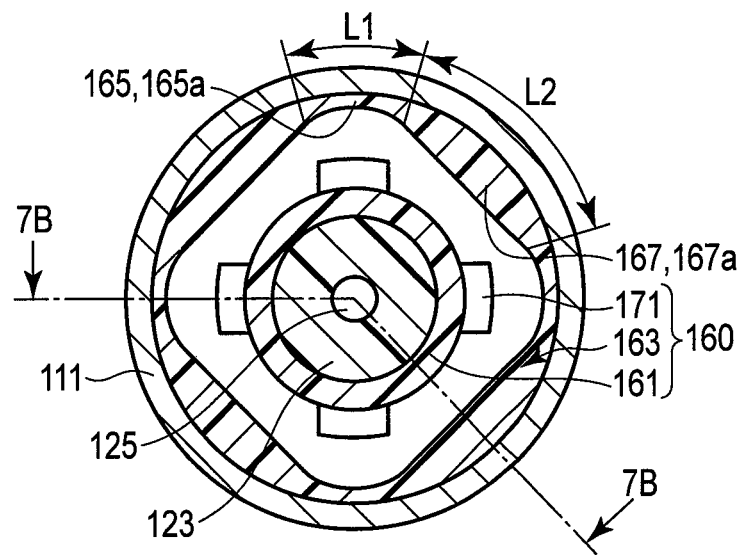
F I G. 7A
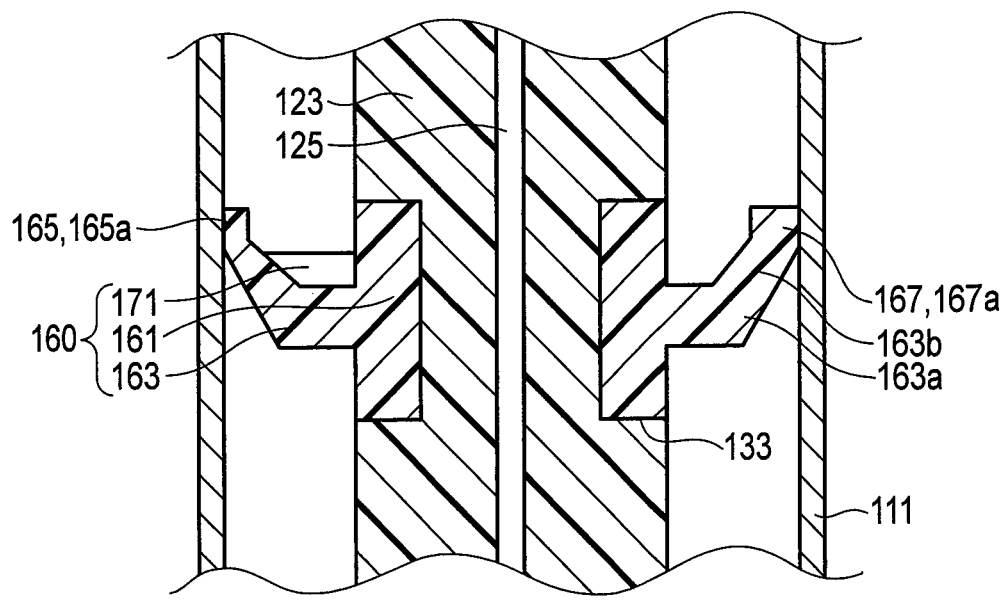
F I G. 7B

ENDOSCOPE CHANNEL SWITCHING APPARATUS

CROSS-REFERENCE TO RELATED APPLICATIONS

This application is a Continuation Application of PCT Application No. PCT/JP2013/062824, filed May 7, 2013 and based upon and claiming the benefit of priority from prior Japanese Patent Application No. 2012-117718, filed May 23, 2012, the entire contents of all of which are incorporated herein by reference.

BACKGROUND OF THE INVENTION

1. Field of the Invention

The present invention relates to an endoscope channel switching apparatus which switches a communicating state of a channel part in an endoscope.

2. Description of the Related Art

Generally, an endoscope comprises an observation window to observe inside of a body cavity. If a body fluid sticks to the observation window, an observation field of view of the observation window narrows. Thus, in order to preserve the field of view, the endoscope is required to implement at least one of a gas supply and a water supply toward the observation window. The endoscope comprises a switching apparatus which switches from one of either the gas supply or water supply to the other. The switching apparatus comprises a piston and a cylinder. As the piston moves in relation to the cylinder, switching occurs from one to the other of the channel parts for gas supply or the channel parts for water supply.

Such an endoscope is disclosed, for example, in Jpn. Pat. Appln. KOKAI Publication No. 9-122069. According to Jpn. Pat. Appln. KOKAI Publication No. 9-122069, a piston is provided with a hemispherical check valve part. The check valve part can be brought into tight contact with an inner circumference of a cylinder to increase airtightness between the piston and the cylinder. The check valve part has a ring shape. In addition, the inner circumference of the check valve part is joined to an outer circumference of the piston so as to allow the piston to penetrate the check valve part. As the piston moves in relation to the cylinder, switching occurs from one to the other of the channel parts for gas supply or the channel parts for water supply.

BRIEF SUMMARY OF THE INVENTION

An aspect of an endoscope channel switching apparatus of the present invention includes a cylinder connected to a plurality of channel parts, and a piston detachably fitted into be inserted in the cylinder, and which switches communication states of the channel parts in accordance with movement of the piston in relation to the cylinder, the apparatus including a check valve unit which is provided on the piston and moves together with the piston in accordance with movement of the piston in relation to the cylinder, wherein the check valve unit comprises a low-strength part and a high-strength part which are provided in the side of a head part of the check valve unit moving, are arranged alternately in circumferential directions of the check valve unit, and have strength levels different from each other.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of the endoscope according to the present invention;

FIG. 3C is a top view of the check valve unit in the gas supply state;

FIG. 4B shows a side view, a top view, and a cross-sectional view in a state in which, a part of the check valve part shown in FIG. 4A in an upper end part side curls back due to sliding resistance;

FIG. 4D is a top view of the check valve unit, showing a state in which a high strength part of the present embodiment prevents curl-back from spreading throughout the entire circumference on an upper end part side;

FIG. 5A shows a top view of the check valve unit in a state in which the length of a low strength part is greater than the length of a high strength part;

FIG. 5B is a top view of the check valve unit shown in FIG. 5A in the gas supply state;

FIG. 7A is a top view of a check valve unit according to the third embodiment; and FIG. 7B shows the periphery of the check valve unit along a line 7B-7B shown in FIG. 7A.

DETAILED DESCRIPTION OF THE INVENTION

Figure 2A:
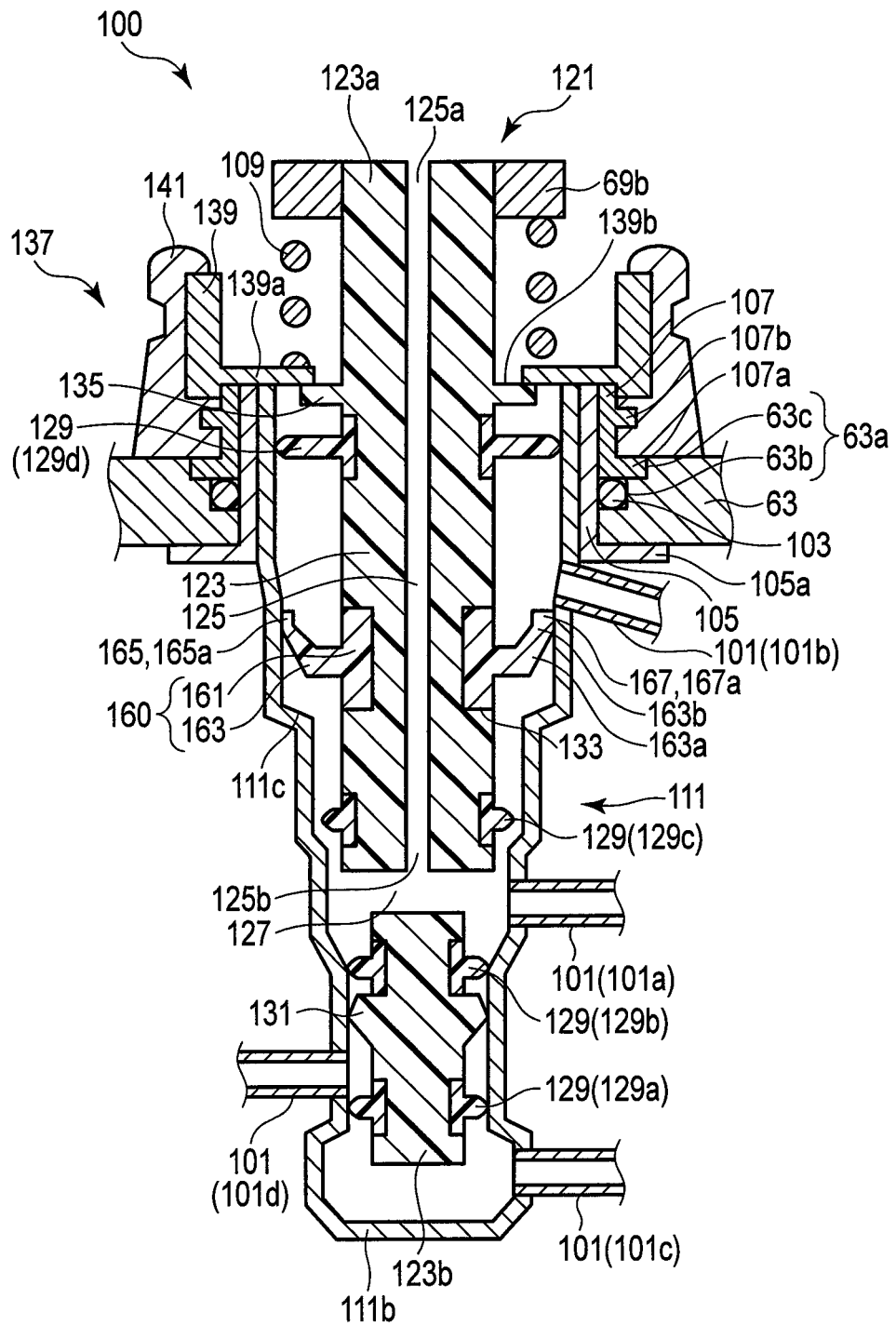
FIG. 2A shows the endoscope channel switching apparatus according to the first embodiment, including a periphery of a check valve unit along a line 2A-2A shown in FIG. 2D.

Hereinafter, embodiments of the present invention will be described in detail in reference to the above listed drawings.

[First Embodiment]
[Configuration]

The first embodiment will be described with reference to FIGS. 1, 2A, 2B, 2C, 2D, 3A, 3B, 3C, 3D, 4A, 4B, and 4C. From several of the drawings, several members are omitted for clarification of illustration.

[Endoscope 1]

As shown in FIG. 1, an endoscope 1 comprises a narrow elongated insertion part 10 inserted into a patient's body cavity, and an operation part 60 which is connected to a proximal end part of the insertion part 10 and operates the endoscope 1.

[Insertion Part 10]

The insertion part 10 comprises a distal-end hard part 21, a bendable part 23, and a flexible tube part 25 in this order toward a proximal end side of the insertion part 10 from a distal end side of the insertion part 10. A proximal end part of the distal-end hard part 21 is connected to a distal end part of the bendable part 23, and a proximal end part of the bendable part 23 is connected to a distal end of the flexible tube part 25.

The distal-end hard part 21 is a distal end part of the insertion part 10 and is hard and does not bend.

The bendable part 23 bends in desired directions, for example, in up, down, left, and right directions in accordance with an operation of a bend operation part 67, described later. As the bendable part 23 bends, the position and orientation of the distal-end hard part 21 change in a manner that illumination light illuminates an observation object and the observation object is captured in an observation field of view.

The flexible tube part 25 has desired flexibility. Therefore, the flexible tube part 25 bends with external force. The flexible tube part 25 is a tubular member extended from a body part 61 of the operation part 60, described later.

[Insertion Part 60]

The operation part 60 comprises the body part 61 from which the flexible tube part 25 is extended, a grip part 63 connected to a proximal end part of the body part 61 and gripped by an operator who operates the endoscope 1, and a universal cord 65 connected to the grip part 63.

[Grip Part 63]

The grip part 63 comprises the bend operation part 67 with which the bendable part 23 is operated to bend. The bend operation part 67 comprises a right/left-bend operation knob 67a to operate the bendable part 23 to bend to the right/left, an up/down-bend operation knob 67b to operate the bendable part 23 to bend up/down, and a fixing knob 67c to fix the position of the bendable part 23 bent.

The grip part 63 further comprises a switch part 69. The switch part 69 comprises a suction switch 69a, and a gas/water supply switch 69b. The suction switch 69a, and the gas/water supply switch 69b are operated by an operator's hand when the grip part 63 is gripped by the operator. The gas/water supply switch 69b is operated when the supply of a fluid from a not-shown gas/water supply tube is performed to ensure an observation field of view of a not-shown imaging unit at the distal-end hard part 21. The fluid includes liquids, such as water, and gases, such as air.

The grip part 63 also comprises various buttons 71 for endoscopic imaging.

[Universal Cord 65]

The universal cord 65 comprises a connector part 65a connected to a not-shown video processor, a not-shown light source apparatus, a gas supply apparatus 81, and a water supply apparatus 83. The video processor, the light source apparatus, the gas supply apparatus 81, and the water supply apparatus 83 are provided, for example, outside the endoscope 1. The gas supply apparatus 81 comprises, for example, the gas supply pump. The gas supply apparatus 81 is connected to the water supply apparatus 83 through a channel part 85. The water supply apparatus 83 comprises a charge tank filled with water to be supplied.

[Endoscope Channel Switching Apparatus (Hereinafter Referred to as a Channel Switching Apparatus 100)]

Next, with reference to FIGS. 2A, 2B, 2C, and 2D, the channel switching apparatus 100 according to the present embodiment will be described. In the following, the term of upper side indicates, for example, outside of the grip part 63, and side of the gas/water supply switch 69b in axial directions of the channel switching apparatus 100. Further, the term of lower side indicates, for example, inside of the grip part 63, and side of the other end part 111b of a cylinder 111 in the axial directions of the channel switching apparatus 100.

As shown in FIG. 2A, the channel switching apparatus 100 comprises the gas/water supply switch 69b as an operation part which is operated when one of a gas supply and a water supply is switched to the other and when gas/water supply is performed as described above, the cylinder 111 to which a plurality of channel parts 101 are connected, and a piston 121 which connects to the gas/water supply switch 69b and is detachably fitted into be inserted in the cylinder 111. The channel switching apparatus 100 switches communicating states of the channel parts 101 by movement of the piston 121 relative to the cylinder 111.

[Cylinder 111]

The cylinder 111 will be described with reference to FIGS. 2A and 2B.

The cylinder 111 has, for example, an approximately cylindrical shape. The cylinder 111 is made of, for example, metal. The cylinder 111 has an opening end part 111a and a closed other end part 111b. The cylinder 111 is tapered from the side of the end part 111a (opening part) toward the side of the other end part 111b (bottom part) along an axial direction of the cylinder 111 in a manner that steps are formed on the cylinder 111. The cylinder 111 comprises a bottom part which is provided at the other end part 111b, is opposed to the opening part of the cylinder 111, and is integral with the circumference of the cylinder 111. The bottom part is smaller than the opening part. Since the cylinder 111 is tapered, the cylinder 111 has a contact face 111c formed on the inner circumference of the cylinder 111 and is oblique to the axial directions of the cylinder 111. The contact surface 111c is provided between an inflow-gas-supply tube part 101a and an outflow-gas-supply tube part 101b described later. An inclination angle of the contact face 111c is not particularly limited. The cylinder 111 as described above is molded, for example, by press work with a deep drawing step. The cylinder 111 needs not to be limited to this example but may be shaped by cutting work. Further, a molding method of the cylinder 111 according to the present embodiment may be applied to a channel switching apparatus for suctioning. As shown in FIG. 2A, an inside diameter of the cylinder 111 at a part connected to an inflow-water-supply tube part 101c is greater than another inside diameter at a part connected to an outflow-water-supply tube part 101d. The part connected to the outflow-water-supply tube part 101d functions as a minimum diameter part where the inside and outside diameters of the cylinder 111 are the smallest.

[Channel Parts 101]

The cylinder 111 comprises holes to communicate with a plurality of channel parts 101. Each one of the channel parts 101 is joined to one of the holes.

Figure 2B:
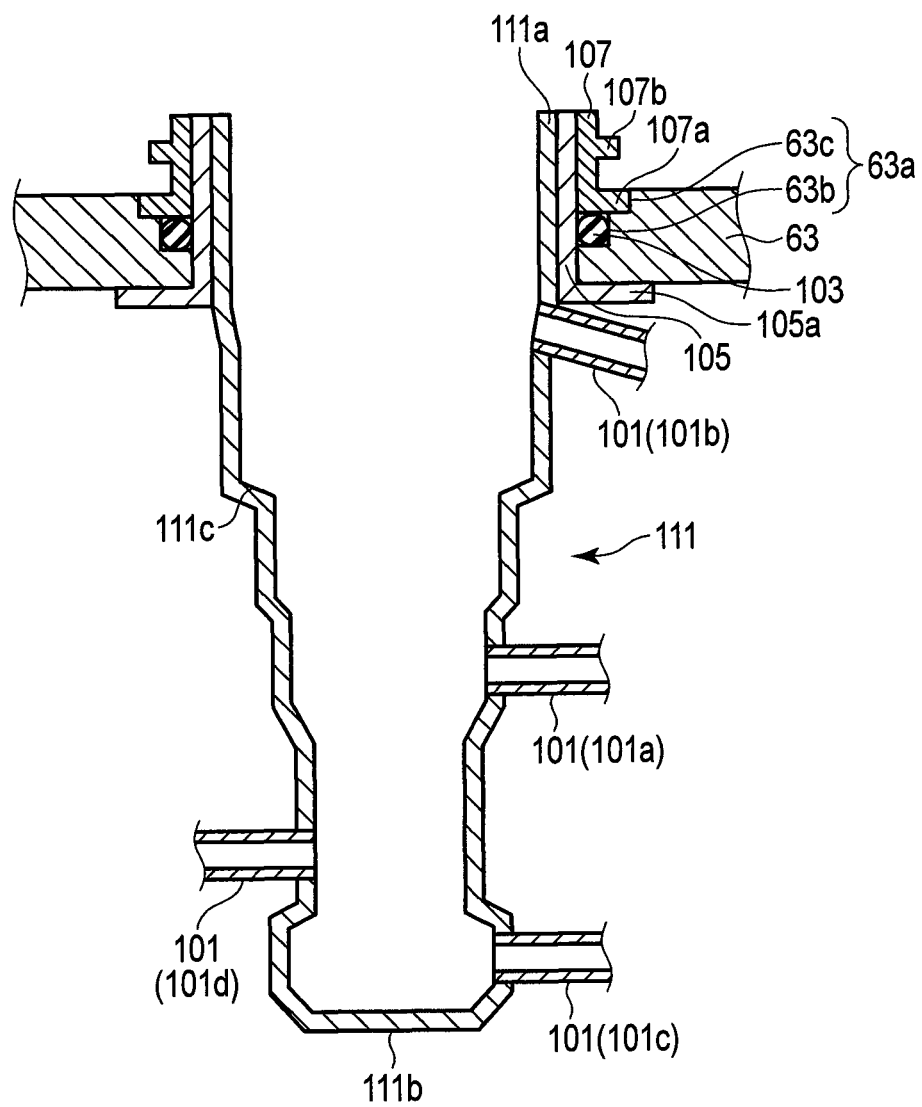
FIG. 2B shows a cylinder.

As shown in FIG. 2B, the plurality of channel parts 101 comprise, for example, the inflow-gas-supply tube part 101a, outflow-gas-supply tube part 101b, inflow-water-supply tube part 101c, and outflow-water-supply tube part 101d. As shown in FIG. 2B, the outflow-gas-supply tube part 101b, inflow-gas-supply tube part 101a, outflow-water-supply tube part 101d, and inflow-water-supply tube part 101c are provided in this order from the one end part 111a toward the other end part 111b.

[Inflow-Air-Supply Tube Part 101a]

The inflow-gas-supply tube part 101a is provided extending from inside of the grip part 63 to inside of the universal cord 65. The inflow-gas-supply tube part 101a is provided along and inside the universal cord 65. The inflow-gas-supply tube part 101a connects to the connector part 65a through the universal cord 65. When the connector part 65a is connected to the gas supply apparatus 81, the inflow-gas-supply tube part 101a connects to the gas supply apparatus 81, and a gas is supplied from the gas supply apparatus 81. The inflow-gas-supply tube part 101a functions as a gas supply tube.

[Outflow-Air-Supply Tube Part 101b]

Along the operation part 60 and insertion part 10, the outflow-gas-supply tube part 101b is provided inside the operation part 60 and inside the insertion part 10. The outflow-gas-supply tube part 101b communicates with a gas/water supply nozzle, not shown, which is provided at the distal-end hard part 21. The outflow-gas-supply tube part 101b supplies a gas supplied from the inflow-gas-supply tube part 101a to the gas/water supply nozzle.

[Inflow-Water-Supply Tube Part 101c]

The inflow-water-supply tube part 101c is provided extending from inside of the grip part 63 to inside of the universal cord 65. The inflow-water-supply tube part 101c is provided along and inside the universal cord 65. Further, the inflow-water-supply tube part 101c connects to the connector part 65a through the universal cord 65. When the connector part 65a is connected to the water supply apparatus 83, the inflow-water-supply tube part 101c connects to the water supply apparatus 83, and is supplied with a liquid from the water supply apparatus 83. The inflow-water-supply tube part 101a functions as a water supply tube.

[Outflow-Water-Supply Tube Part 101d]

Along the operation part 60 and insertion part 10, the outflow-water-supply tube part 101d is provided inside the operation part 60 and inside the insertion part 10. The outflow-water-supply tube part 101d communicates with a gas/water supply nozzle, not shown, which is provided at the distal-end hard part 21. The outflow-water-supply tube part 101d supplies the gas/water supply nozzle with the liquid supplied from the inflow-water-supply tube part 101c.

[Position of Cylinder 111]

As shown in FIG. 2B, the cylinder 111 is detachably inserted in a hole part 63a provided at the grip part 63, and is fixed to the grip part 63. The outside diameter of the hole part 63a is greater than the outside diameter of the cylinder 111. This hole part 63a comprises a lower annular groove part 63b where an O-ring 103 is provided, and an upper annular groove part 63c provided in an upper side of the lower annular groove part 63b and fitted into a lower flange part 107a of a metallic cap 107 described later. The lower annular groove part 63b is smaller than the upper annular groove part 63c, and is provided to be coaxial with the upper annular groove part 63c. The lower annular groove part 63b communicates with the upper annular groove part 63c in thickness directions of the grip part 63.

As also shown in FIG. 2B, the cylinder 111 is fixed to the grip part 63 by a press member 105 and the metallic cap 107 through the hole part 63a.

The press member 105 has a ring shape, and an inner circumferential surface of the press member 105 is joined to an outer circumferential surface of the one end part 111a. Further, the press member 105 comprises the flange part 105a formed outward in radial directions of the press member 105. The flange part 105a is provided inside the grip part 63. Further, an inner circumferential surface of the hole part 63a and an outer circumferential surface of the press member 105 each has a screw-thread groove not shown. Since the flange part 105a is provided, the press member 105 is screwed into the hole part 63a outward from inside of the grip part 63. When the press member 105 is screwed into the hole part 63a, the flange part 105a is caught on the inner surface side of the grip part 63. The cylinder 111 is thereby prevented from dropping from the grip part 63. At this time, a part of the outer circumferential surface of the press member 105 is brought into contact with the O-ring 103.

An inner circumferential surface of the metallic cap 107 also comprises a screw-thread groove, and the metallic cap 107 is screwed onto the press member 105. Also, the metallic cap 107 comprises the lower flange part 107a which fits into the upper annular groove part 63c, and an upper flange part 107b provided in the upper side of the lower flange part 107a in axial directions of the metallic cap 107. The lower flange part 107a and the upper flange part 107b are formed outward in radial directions of the metallic cap 107. The lower flange part 107a and the upper flange part 107b are formed outside the metallic grip 107. When the lower flange part 107a fits into the upper annular groove part 63c, the flange part 105a and the lower flange part 107a sandwich the grip part 63 from upper and lower sides in axial directions of the cylinder 111, thereby fixing the cylinder 111 to the grip part 63.

When the metallic cap 107 is screwed into the member 105, the lower flange part 107a fits, into the upper annular groove part 63c, thereby compressing O-ring 103. In this manner, penetration of gases and liquids from outside to inside of the endoscope 1 is prevented. That is, watertightness and airtightness are ensured.

[Piston 121]

Next, the piston 121 will be described with reference to FIGS. 2A, 2C, and 2D.

The piston 121 comprises a hard piston shank 123 as a body part of the piston 121, which is narrower than the cylinder 111, and an attachment part 137 with which the piston shank 123 is attached to the grip part 63.

[Piston Shank 123]

The piston shank 123 has a long narrow shape along axial directions of the piston 121. The piston shank 123 is inserted into the cylinder 111, and is movable along the axial directions of the cylinder 111 in relation to the cylinder 111. Since the piston shank 123 is narrower than the cylinder 111, a flow channel part where a fluid flows is formed between the outer circumferential surface of the piston shank 123 and the inner circumferential surface of the cylinder 111.

Figure 2C:
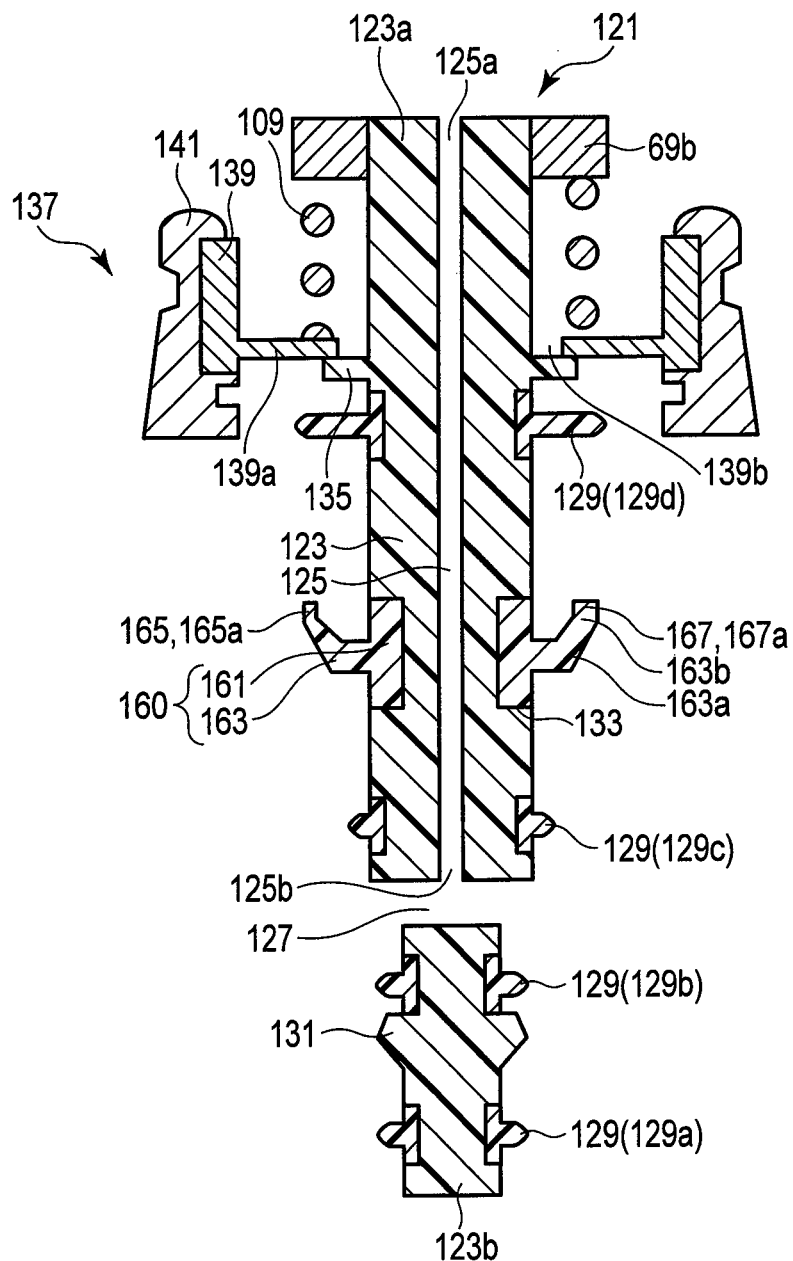
FIG. 2C shows a piston including the periphery of the check valve unit along a line 2C-2C shown in FIG. 2D.

As shown in FIG. 2C, the piston shank 123 comprises an end part 123a is provided so as to be surrounded by the gas/water supply switch 69b and provided outside the cylinder 111 (grip part 63), and another end part 123b provided inside the cylinder 111. The end part 123a is, for example, screwed in the gas/water supply switch 69b.

[Communication Channel 125 and Through-Hole 127]

Further as shown in FIG. 2C, the piston shank 123, comprises a communication channel 125 provided inside the piston shank 123 on the center axis of the piston shank 123, and a through-hole 127 provided in the side of the other end part 123b of the piston shank 123 and penetrating the piston shank 123 in a radial direction of the piston shank 123. The communication channel 125 comprises an end part 125a open at the end part 123a of the piston shank 123, and the other end part 125b communicating with the through-hole 127. Thus, the communication channel 125 communicates with the exterior. Further, the communication channel 125 does not penetrate the piston shank 123 but communicates with the exterior and the through-hole 127.

Figure 3A:
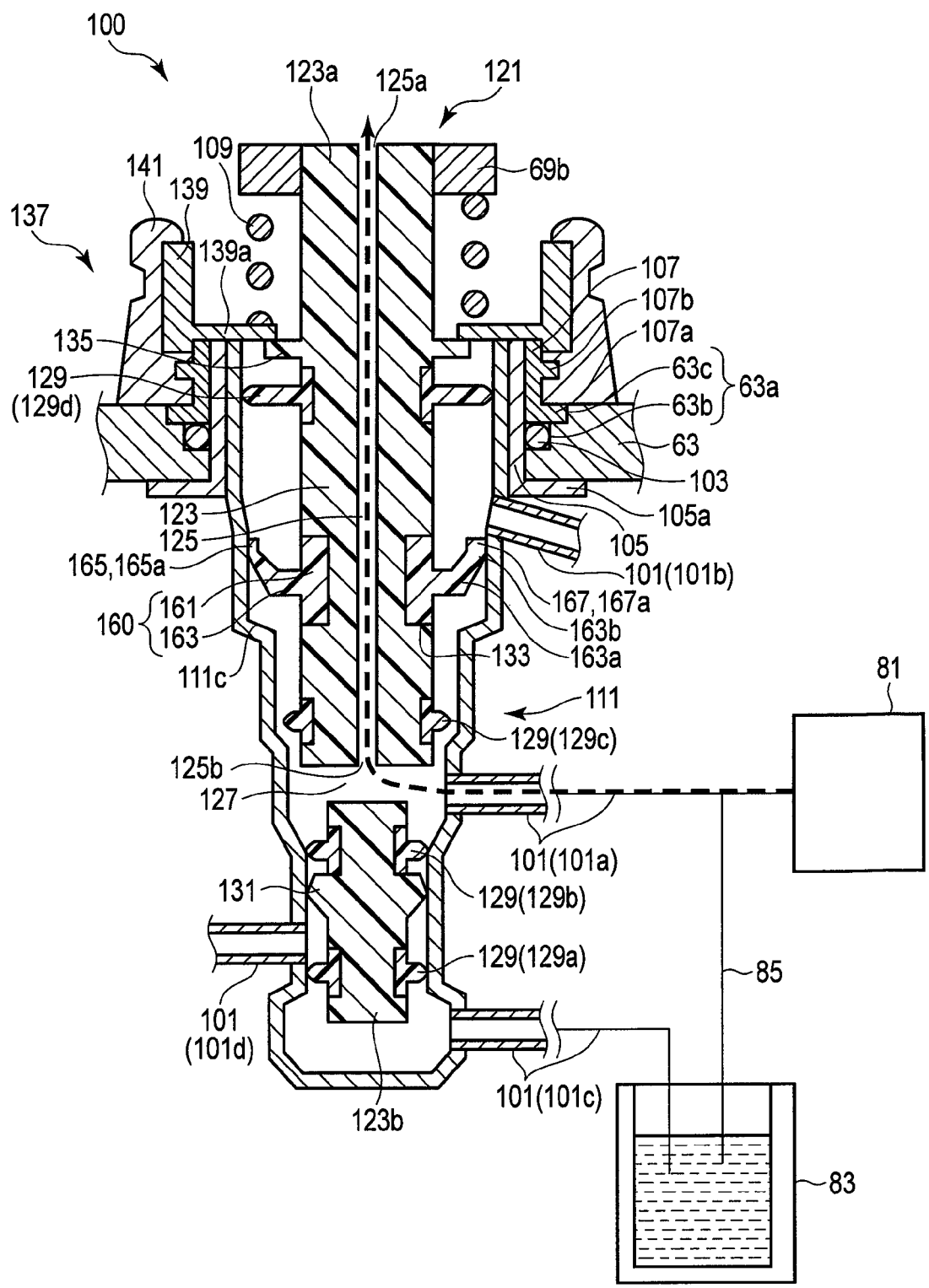
FIG. 3A shows the endoscope channel switching apparatus in a not-operated state, including the periphery of the check valve unit along a line 3A-3A shown in FIG. 2D.

As shown in FIGS. 2A and 3A, when the end part 125a is opened, the communication channel 125 and the through-hole 127 function as a flow channel part for emitting a gas supplied into the cylinder 111 from the inflow-gas-supply tube part 101a, to the exterior through the end part 125a.

Figure 3B:
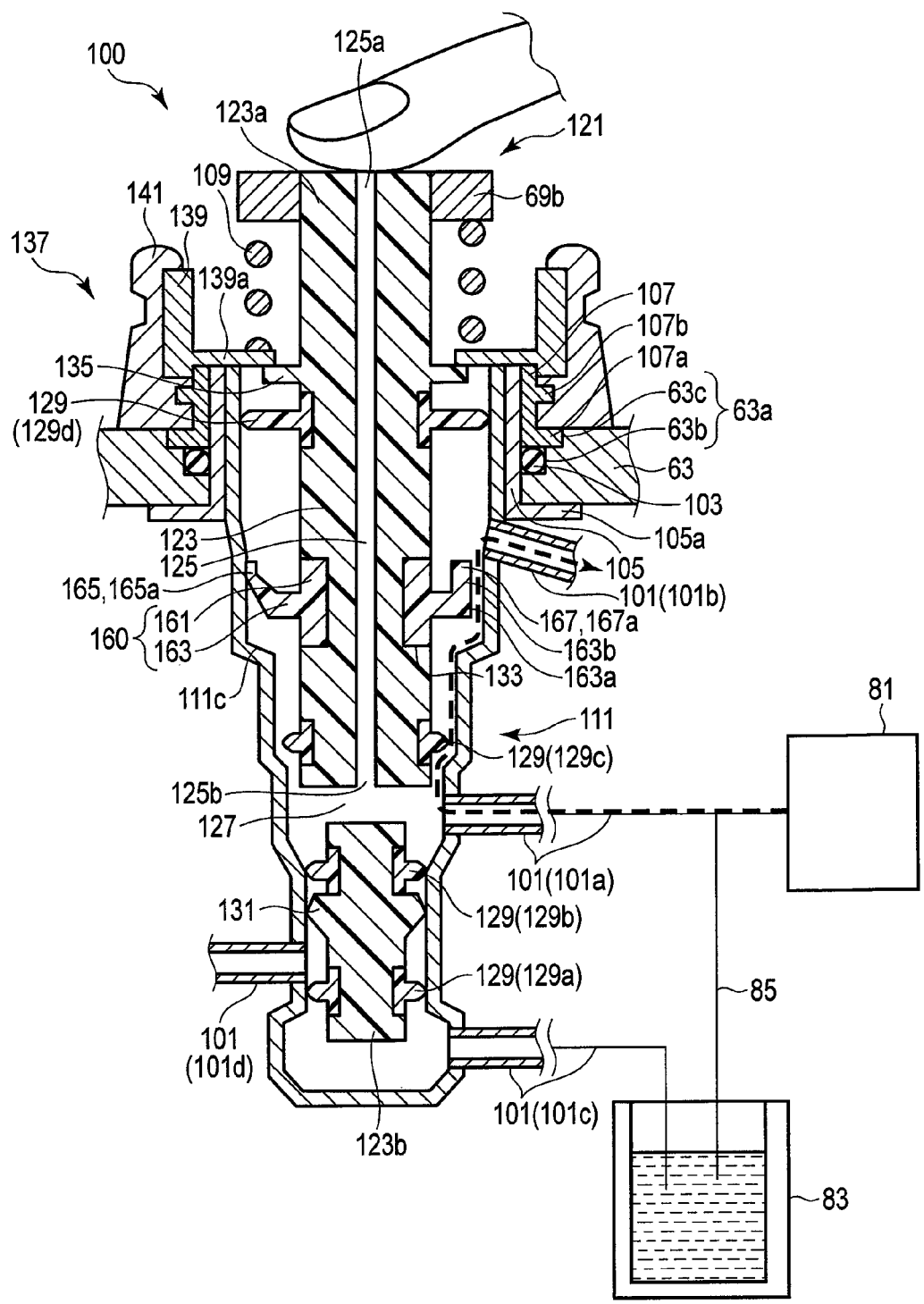
FIG. 3B shows the endoscope channel switching apparatus in a gas supply state, including the periphery of the check valve unit along a line 3B-3B shown in FIG. 3C.

Further as shown in FIG. 3B, when the end part 125a is closed with a finger for example, the through-hole 127 functions as a flow channel part for emitting the gas supplied into the cylinder 111 from the inflow-gas-supply tube part 101a, to the inflow-gas-supply tube part 101b.

In the piston shank 123, a part above the through-hole 127 is thicker than a part below the through-hole 127. That is, a part of the piston shank 123 where the communication channel 125 is provided is thicker than a part where the communication channel 125 is not provided.

[Sealing Members 129]

As shown in FIGS. 2A and 2C, the piston shank 123 further comprises a plurality of sealing members 129 which are in tight contact with the inner circumferential surface of the cylinder 111 and achieves sealing between the piston shank 123 and the cylinder 111 when the piston shank 123 is inserted into the cylinder 111. The sealing members 129 each comprise packing made of, for example, an elastic body such as rubber or an elastomer. The sealing members 129 each have, for example, a ring shape.

The sealing members 129 comprise, for example, sealing members 129a, 129b, 129c, and 129d. The sealing member 129a is, for example, provided at the other end part 123b of the piston shank 123. The sealing member 129a is provided, for example, between the other end part 123b of the piston shank 123 and the through-hole 127 in axial directions of the piston shank 123. The sealing member 129c is provided, for example, between the end part 123a of the piston shank 123 and the through-hole 127 in the axial directions of the piston shank 123. The sealing member 129d is provided, for example, in a side closer to the end part 123a of the piston shank 123 than the sealing member 129c in axial directions of the piston shank 123.

The sealing members 129a and 129b have the same shape as each other, and are provided in the lower side of the through-hole 127. Therefore, the sealing members 129a and 129b provided on the piston shank 123 have the same outside diameters as each other.

The sealing members 129c and 129d are provided in the upper side of the through-hole 127. Therefore, the sealing members 129c and 129d provided on the piston shank 123 have greater outside diameters than the outside diameter of the sealing member 129a. The outside diameter of the sealing member 129d is greater than the outside diameter of the sealing member 129c.

The piston shank 123 and the sealing members 129 are welded to each other in a manner that make tight contact with each other without any gap between interface of the piston shank 123 and interface of the sealing members 129, neither dirt nor bacterial contamination sticks to the interfaces but cleanliness improves. To achieve this welding, the piston shank 123 and the sealing member members 129 are formed by, for example, double molding or insertion molding. Specifically, the piston shank 123 is provided, for example, in a not shown metal mold for molding the sealing members 129. Next, the sealing members 129 are provided in a metal mold, and are welded by heat. This heat melts the surface of the piston shank 123. The sealing member 129 is solidified by cooling and is welded to the piston shank 123. Thus, the piston shank 123 and the sealing member 129 are integrated together.

The piston shank 123 and the sealing members 129 are washed with, for example, a chemical, and therefore are formed of a material having chemical resistance. The piston shank 123 is formed of, for example at least one of polypropylene, polycarbonate, nylon, sulfone-based resin such as polysulfone or polyphenylsulfone, liquid crystal polymer, modified polyphenylene ether, and polyether, ether, or ketone. The sealing members 129 each are formed of, for example, at least one of silicone rubber, and styrene-based/olefin-based elastomer.

[Guide Member 131, Notch Part 133, and Drop Prevention Part 135]

Further as shown in FIG. 2C, the piston shank 123 further comprises a guide member 131 provided between the sealing member 129a and the sealing member 129b in axial directions of the piston shank 123, a notch part 133 provided between the sealing member 129c and the sealing member 129d in the axial directions of the piston shank 123, and a drop prevention part 135 provided in a side closer to the end part 123a than the sealing member 129d in the axial directions of the piston shank 123.

[Guide Member 131]

The guide member 131 is integral with the piston shank 123. The guide member 131 makes contact with the inner circumferential surface of the cylinder 111 in order to prevent the piston shank 123 from moving in radial directions of the cylinder 111 in relation to the cylinder 111. The guide member 131 guides the piston shank 123 in a manner that the piston shank 123 is movable along axial directions of the cylinder 111 in the cylinder 111 when the piston shank 123 is inserted into the cylinder 111. When the piston shank 123 is inserted into the cylinder 111, the guide member 131 slides on the inner circumferential surface of the cylinder 111 along the axial directions of the cylinder 111.

[Notch Part 133]

The notch part 133 is formed in a circular ring shape. A check valve unit 160 described later is provided at the notch part 133.

[Drop Prevention Part 135]

The drop prevention part 135 has, for example, a ring shape and is integral with the piston shank 123. The drop prevention part 135 is brought into contact with a bottom surface 139a of a drop prevention contact part 139 described later, provided at the attachment 137.

[Attachment Part 137]

As shown in FIG. 2C, the attachment 137 is provided in the side of the end part 123a of the piston shank 123. The attachment part 137 comprises a hard drop prevention contact part 139 which has a cylindrical shape, allows the piston shank 123 to insert into, and is provided to surround the end part 123a of the piston shank 123 and a soft attachment body part 141 which has a cylindrical shape and is provided to surround the drop prevention contact part 139.

[Drop Prevention Contact Part 139]

The drop prevention contact part 139 is provided so as to make tight contact with the entire inner circumferential surface of the attachment body part 141. The drop prevention contact part 139 has a cylindrical shape which has a bottom face 139a in one side. The bottom face 139a comprises an insertion hole 139b into which the piston shank 123 is inserted. The bottom face 139a makes contact with the drop prevention part 135. The bottom face 139a is provided in the lower side of the gas/water supply switch 69b in the axial directions of the piston 121. When the channel switching apparatus 100 is assembled, the bottom face 139a is brought into contact with the end part 111a of the cylinder 111, an edge part of the press member 105, and an edge part of the metallic cap 107.

[Urging Member 109]

An urging member 109 is provided between the bottom face 139a and the gas/water supply switch 69b in axial directions of the piston 121. The urging member 109 is provided so as to be wound around the one end part 123a of the piston shank 123. The urging member 109 comprises, for example, a coil spring made of metal. The urging member 109 can expand and contract in the axial directions of the piston 121. The urging member 109 has urging force which urges the piston shank 123 upward through the gas/water supply switch 69b, and also urges the drop prevention contact part 139 (bottom face 139a) downward (toward the drop prevention part 135). In a natural state of the urging member 109, the urging member 109 urges the piston shank 123 upward through the gas/water supply switch 69b, and also urges the drop prevention contact part 139 (bottom face 139a) downward (toward the drop prevention part 135). At this time, the drop prevention part 135 and the bottom face 139a are brought into contact with and pressed to each other. The drop prevention part 135 thereby prevents the piston shank 123 from slipping off from the attachment 137. The urging member 109 is surrounded by the drop prevention contact part 139.

[Attachment Body Part 141]

The attachment-body part 141 comprises, for example, rubber. The attachment body part 141 engages with the lower flange part 107a of the metallic cap 107 and is provided on the outer circumferential surface of the grip part 63.

[Check Valve Unit 160]

Figure 2D:
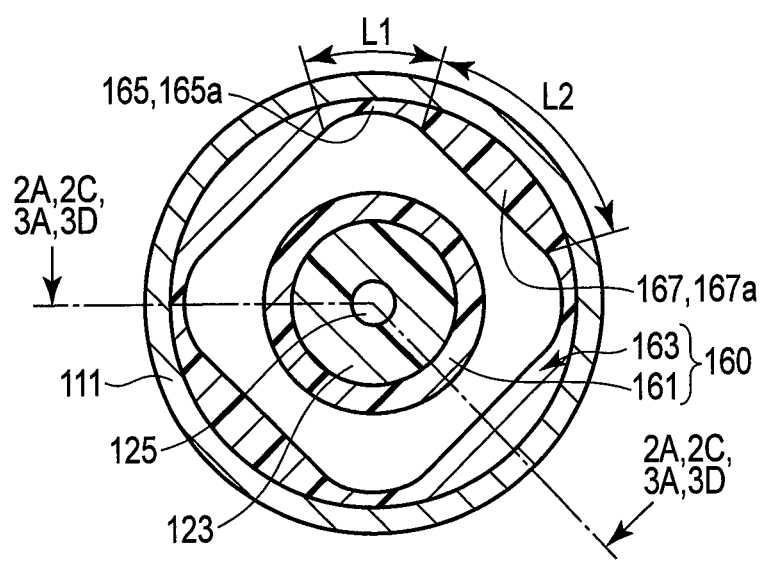
FIG. 2D is a top plan of the check valve unit.

As shown in FIGS. 2A, 2C, and 2D, the channel switching apparatus 100 comprises a check valve unit 160 provided at the notch part 133 of the piston 121.

The check valve unit 160 opens/closes in accordance with internal pressure inside the cylinder 111, and is brought into tight contact with or made to separate from the inner circumferential surface of the cylinder 111 in accordance with the opening/closing. Further, the check valve unit 160 achieves sealing between the cylinder 111 and the piston shank 123 by the tight contact. The check valve unit 160 is provided on the piston shank 123 through the notch part 133, and moves together with the piston shank 123 in accordance with movement of the piston shank 123 relative to the cylinder 111.

The check valve unit 160 as described above comprises a body part 161 which has a cylindrical shape to be embedded in the notch part 133, and a check valve part 163 which has a tubular shape whose diameter decreases gradually from the upper side to the lower side and is connected to be integral with the body part 161.

The body part 161 and the check valve part 163 each are formed of, for example, an elastic body such as rubber or an elastomer in the same manner as the sealing member 129.

[Body Part 161]

The body part 161 is embedded in the notch part 133 and is bonded to the piston shank 123. Therefore, when the piston shank 123 moves in relation to the cylinder 111, the body part 161 moves with the piston shank 123.

As shown in FIGS. 2A and 2C, the outside diameter of the body part 161 is approximately the same as the outside diameter of the piston shank 123. Therefore, when the body part 161 is embedded in the notch part 133, the outer circumferential surface of the body part 161 is on the same planar surface as the outer circumferential surface of the piston shank 123.

[Check Valve Unit 163]

As shown in FIGS. 2A and 2C, the check valve part 163 has a shape which is substantially closed toward the lower side and is opened toward the upper side. The shape as described above shows, for example, any one of a substantially umbrella-like shape, a hollow truncated cone shape, a hemispherical dome shape, and a hollow parabolic shape. Therefore, the check valve part 163 has a diameter which gradually decreases from the side of an upper end part 163b of the check valve part 163 toward the side of a lower end part 163a of the check valve part 163 in an axial direction of the check valve part 163.

As shown in FIGS. 2A and 2C, the check valve part 163 has the lower end part 163a which is provided in the lower side and is substantially closed, and the upper end part 163b which is provided in the upper side and is opened toward the upper side. The lower end part 163a and the upper end part 163b each have a hollow shape, e.g., a ring shape.

As shown in FIGS. 2A and 2C, the lower end part 163a is integral with the lower end part side of the body part 161, and is fixed to the lower end part side of the outer circumferential surface of the body part 161. Thus, the check valve part 163 is integral with the body part 161. Further, the lower end part 163a functions as a root part of the check valve part 163, as a fixed end, and also as a closed end.

As shown in FIGS. 3A and 3B, the upper end part 163b opens/closes in accordance with internal pressure inside the cylinder 111, and is brought into tight contact with or made to separate from the inner circumferential surface of the cylinder 111 in accordance with the opening/closing. Further, the upper end part 163b achieves sealing between the cylinder 111 and the piston shank 123 by the tight contact. Thus, the lower end part 163a functions as a distal end part of the check valve part 163, as a free end, and also as an open end.

Figure 3D:
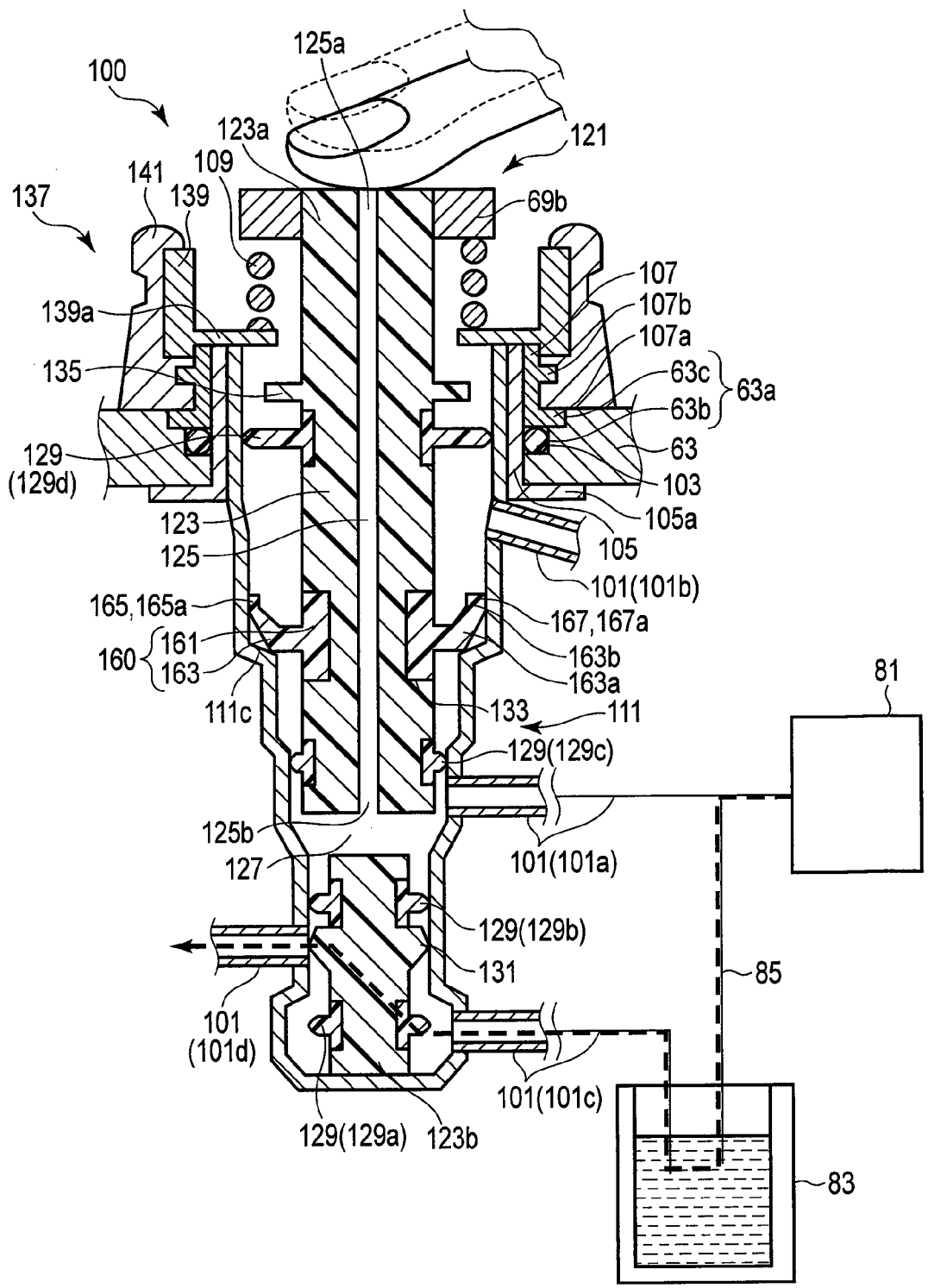
FIG. 3D shows the endoscope channel switching apparatus in a water supply state, including the periphery of the check valve unit along a line 3D-3D shown in FIG. 2D.

Also as described above, the body part 161 is bonded to the piston shank 123, and the check valve part 163 is integral with the body part 161. Therefore, as shown in FIGS. 3A and 3D, when the piston shank 123 moves in relation to the cylinder 111, the check valve part 163 including the body part 161 moves together with the piston shank 123. When a state as shown in FIG. 3A switches to a state as shown in FIG. 3D thereby moving the lower end part 163a downward, the lower end part 163a functions as a head (distal end) part of the check valve unit 160. When the state as shown in FIG. 3D switches to the state as shown in FIG. 3A thereby moving the lower end part 163a upward, the upper end part 163a functions as a head (distal end) part of the check valve unit 160 moving. Particularly when a water supply state shown in FIG. 3D described later switches to a non-operation state shown in FIG. 3A, the upper end part 163b is brought into tight contact with the inner circumferential surface of the cylinder 111 and therefore slides upward on the inner circumferential surface of the cylinder 111. Therefore, the upper end part 163b functions as a head part of the check valve unit 160 sliding upward.

In order that the lower end part 163a of the check valve part 163 is provided on the side of the other end part 123b and the upper end part 163b of the check valve part 163 is provided on the side of the 123a, the front surface of the check valve part 163 faces the side of the other end part 123b and the rear surface of the check valve part 163 faces the end part 123a.

[Low-Strength Part 165 and High-Strength Part 167]

Further as shown in FIGS. 2C and 2D, the check valve unit 160 comprises a low-strength part 165 and a high-strength part 167 which are provided on the side of the upper end part 163b of the check valve part 163 and which have respectively different strengths. The low-strength part 165 has low strength and rigidity, while the high-strength part 167 has high strength and rigidity.

As shown in FIG. 2C, the low-strength part 165 and the high-strength part 167 are provided on the side of the upper end part 163b of the check valve part 163 rather than on the side of the lower end part 163a of the check valve part 163. The low-strength part 165 and the high-strength part 167 are integral with the check valve part 163 on the side of the upper end part 163b. Therefore, the low-strength part 165 and the high-strength part 167 are formed of, for example, elastic members.

As shown in FIG. 2D, the low-strength part 165 and the high-strength part 167 are provided in a plurality to be equal in number, and are arranged alternately in circumferential directions of the check valve unit 160. For example, four low-strength parts 165 and four high-strength parts 167 are provided. The low-strength parts 165 and the high-strength parts 167 are integral with each other, and are connected mutually in the circumferential directions of the check valve unit 160. The low-strength parts 165 and the high-strength parts 167 are smoothly continuous to one another in the circumferential directions of the check valve unit 160 with no difference in the levels formed between one another. In the circumferential directions of the check valve unit 160, for example, the length L1 of each low-strength part 165 is shorter than the length L2 of each high-strength parts 167.

Thus, a variation in strength is caused by the low-strength parts 165 and the high-strength parts 167 in the side of the upper end part 163b. In other words, in the side of the upper end part 163b, there is a variation in strength in circumferential directions of the check valve unit 160 due to the low-strength parts 165 and the high-strength parts 167.

[Thin Parts 165a and Thick Parts 167a]

As shown in FIG. 2C and FIG. 2D, the low-strength parts 165 comprise, for example, thin parts 165a. In the upper end part 163b of the check valve part 163, the thin parts 165a are formed as the thickness of one part of the upper end part 163b decreases to be smaller than the thickness of the other part of the upper end part 163b. Also, the thin parts 165a are thinner than, for example, the lower end part 163a of the check valve part 163.

As also shown in FIG. 2C and FIG. 2D, the high-strength parts 167 comprise, for example, thick parts 165a. In the upper end part 163b of the check valve part 163, the thick parts 167a are formed as the thickness of one part of the upper end part 163b increases to be thicker than the thickness of the other part of the upper end part 163b. Therefore, the thick parts 167a are relatively thicker than the thin parts 165a. The thick parts 167a are thicker than, for example, the lower end part 163a of the check valve part 163. As has been described above, the low-strength parts 165 and the high-strength parts 167 are smoothly continuous to one another in circumferential directions of the check valve unit 160 with no difference in the levels formed between one another. Therefore, as shown in FIG. 2D, the thick parts 167a and the thin parts 165a are smoothly continuous to one another in the circumferential directions of the check valve unit 160 with no difference in the levels formed between one another. Also as shown in FIG. 2D, each of the thick parts 167a gradually thickens, for example, from two ends of the thick part 167a which are in contact with the thin parts 165a, toward the center part of the thick part 167a in the circumferential directions of the check valve unit 160.

Thus, the thickness in the side of the upper end part 163b varies in the circumferential directions of the check valve unit 160 due to the thin parts 165a and the thick parts 167a.

As shown in FIG. 2C and FIG. 2D, the thin parts 165a and thick parts 167a are provided on the inside of the inner circumferential surface in the side of the upper end part 163b. Therefore, the thick parts 167a are formed to be convex from the inner circumferential surface on the side of the upper end part 163b.

Further, as shown in FIG. 2A, FIG. 2D, FIG. 3A, and FIG. 3B, when the check valve unit 160 is in a natural state, when the upper end part 163b of the check valve part 163 is closed under pressure and separated from the inner circumferential surface of the cylinder 111, or when the check valve part 163 is opened with the upper end part 163b of the check valve part 163 made in tight contact with the inner circumferential surface of the cylinder 111, the thick parts 167a are of such thickness as not to allow the thick parts 167a to make contact with the outer circumferential surface of the body part 161. This feature also applies to the thin parts 165a in the same manner.

When the check valve unit 160 is in the natural state, the outside diameter of the upper end part 163b is uniform. Also when the check valve unit 160 is in the natural state, the inside diameter of the upper end part 163b differs between the thick parts 167a and the thin parts 165a.

Also when the check valve unit 160 is in the natural state, the outer circumferential surface of the upper end part 163b has, for example, a cylindrical shape. Also when the check valve unit 160 is in the natural state, the inner circumferential surface of the upper end part 163b has, for example, an approximately rectangular shape with four round corners.

The edge of the upper end part 163b is larger than the inside diameter of the cylinder 111 in the natural state. Therefore, when the piston shank 123 is inserted in the cylinder 111, as shown in FIGS. 2A, 3A, and 3D, the edge of the upper end part 163b is compressed by the cylinder 111 and is brought into tight contact with the inner circumferential surface of the cylinder 111 due to the compression. In this manner, the check valve part 163 achieves sealing between the cylinder 111 and the piston shank 123.

Also, as shown in FIG. 3B, if the end part 125a of the communication channel 125 is closed, for example, by a finger with a gas supplied into the cylinder 111 from the inflow-gas-supply tube part 101a, the internal pressure inside the cylinder 111 increases, and the high-strength parts 167 (thick parts 167a) in the upper end part 163b of the check valve part 163 close and are made apart from the inner circumferential surface of the cylinder 111. At this time, space between the cylinder 111 and the piston shank 123 functions as a flow channel for supplying the outflow-gas-supply tube part 101b with the gas supplied into the cylinder 111 from the inflow-gas-supply tube part 101a.

Thus, at the upper end part 163b, the high-strength parts 167 open/close in accordance with the internal pressure inside the cylinder 111, and are brought into tight contact with or made to separate from the inner circumferential surface of the cylinder 111 in accordance with the opening/closing.

The check valve unit 160 opens/closes in accordance with the internal pressure inside the cylinder 111. When the check valve unit 160 closes, at least a part of the check valve unit 160 is made to separate from the inner circumferential surface of the cylinder 111. Further, when the check valve unit 160 opens, the check valve unit 160 is brought into tight contact with the inner circumferential surface of the cylinder 111 and thereby achieves sealing between the cylinder 111 and the piston 121.

Though described later, at the upper end part 163b, at least either or both of the high-strength parts 167 (thick parts 167a) and the low-strength parts 165 (thin parts 165a) need to be opened and closed by internal pressure.

[Assembly Method]

Next, with reference to FIGS. 2A, 2C, and 2D, the channel switching apparatus 100 according to the present embodiment will be described.

(Step 1/FIG. 2C)

As shown in FIG. 2C, the attachment part 137 is assembled in a manner that the drop prevention contact part 139 makes tight contact with the entire inner circumferential surface of the attachment body part 141.

Next, the attachment part 137 is attached to the piston shank 123 in a manner that the piston shank 123 inserted through the insertion hole 139b in the bottom face 139a and the bottom face 139a of the drop prevention contact part 139 makes contact with the drop prevention part 135.

Further, the end part 123a is screwed in the gas/water supply switch 69b in a manner that the urging member 109 is wound in the end part 123a of the piston shank 123 and the urging member 109 is arranged between the bottom face 139a and the gas/water supply switch 69b. At this time, the urging member 109 urges the piston shank 123 upward through the gas/water supply switch 69b, and also urges the drop prevention contact part 139 (bottom face 139a) downward (toward the drop prevention part 135). Further, the drop prevention part 135 and the bottom face 139a of the drop prevention contact part 139 are brought into contact with and pressed to each other.

In this manner, the piston 121 is assembled.

Assembly of the attachment 137 and assembly of the piston 121 need not be limited to the manners as described above.

In Step 1, the check valve part 163 unit is in a natural state.

(Step 2/FIG. 2A)

Next, as shown in FIG. 2A, the piston shank 123 is pressed into the cylinder ill in a manner that: the upper flange part 107b engages with the attachment body part 141; the attachment body part 141 is brought into contact with the outer circumferential surface of the grip part 63; the bottom face 139a of the drop prevention contact part 139 is brought into contact with the end part 111a of the cylinder 111, the edge part of the press member 105, and the edge part of the metallic cap 107; and the check valve unit 160 is arranged between the contact surface 111c and the outflow-gas-supply tube part 101b in the axial directions of the channel switching apparatus 100. In this manner, the channel switching apparatus 121 is assembled.

This Step 2 indicates one of a non-operation a state in which gas/water supply is not performed and the channel switching apparatus 100 is not operated, and a gas-supply state in which the channel switching apparatus 100 is operated and gas supply is performed.

[Operation Method]

Next, with reference to FIGS. 3A, 3B, 3C, 3D, 4A, 4B, and 4C, descriptions will be made of an operation method of the channel switching apparatus 100 including the check valve unit 160, according to the present embodiment. FIG. 3A corresponds to Step 2 and FIG. 2A.

[Non-Operation State]

The non-operation state shown in Step 2 will be described with reference to FIG. 3A.

As shown in FIG. 3A, the sealing member 129d is provided in the upper side than the outflow-gas-supply tube part 101b and in tight contact with the inner circumferential surface of the cylinder 111, and achieves sealing between the cylinder 111 and the piston shank 123. Further, the check valve unit 160 is provided between the contact surface 111c and the outflow-gas-supply tube part 101b. The check valve part 163 is open. The upper end part 163b of the check valve part 163 is in tight contact with the inner circumferential surface of the cylinder 111, and achieves sealing between the cylinder 111 and the piston shank 123. Therefore, inside space of the cylinder 111 on the side of the outflow-gas-supply tube part 101b is sealed by the sealing member 129d and the check valve part 163.

Further, the sealing parts 129a and 129b are in tight contact with the inner circumferential surface of the cylinder 111, and achieve sealing between the cylinder 111 and the piston shank 123. The sealing member 129a is provided between the inflow-water-supply tube part 101c and the outflow-water-supply tube part 101d. The sealing member 129b is provided between the outflow-water-supply tube part 101d and the inflow-water-supply tube part 101a. In this manner, the inside space of the cylinder 111 on the side of the inflow-water-supply tube part 101c is sealed by the sealing member 129a. Also, the inside space of the cylinder 111 on the side of the outflow-water-supply tube part 101d is sealed by the sealing members 129a and 129b.

The one end part 125a is open, and the communication channel 125 communicates to the exterior. Further as described previously, the upper end part 163b of the check valve part 163 is in tight contact with the inner circumferential surface of the cylinder 111, and the sealing member 129b is in tight contact with the inner circumferential surface of the cylinder 111. In this manner, the inflow-gas-supply tube part 101a communicates with the exterior through the through-hole 127 and the communication channel 125. Therefore, a gas is supplied from the gas supply apparatus 81, and emitted externally through the inflow-gas-supply tube part 101a, through-hole 127, and communication channel 125.

The sealing member 129c is provided between the outflow-gas-supply tube part 101b and the inflow-water-supply tube part 101c, is apart from the inner circumferential surface of the cylinder 111, and does not achieve sealing between the cylinder 111 and the piston shank 123.

[Switch from Non-Operation State to Air Supply State]

Next, the gas supply state shown in Step 2 will be described with reference to FIG. 3B.

The grip part 63 is gripped by the operator from the state shown in FIG. 3A. Further, as shown in FIG. 3B, the end part 125a which is opening is closed by an operator's finger. A gas supplied to inside of the cylinder 111 and the communication channel 125 from the inflow-gas-supply tube part 101a is filled in the inside of the cylinder 111 including the communication channel 125. At this time, the gas flows also into the side of the check valve part 163. Pressure increases inside the cylinder 111. In this manner, the check valve part 163 substantially closes in accordance with an increase in pressure.

At this time, as shown in FIGS. 3B and 3C, at the upper end part 163b of the check valve part 163, the high-strength parts 167 separate from the inner circumferential surface of the cylinder 111, and the low-strength parts 165 are brought into tight contact with the inner circumferential surface of the cylinder 111.

Therefore, as shown in FIG. 3B, a gas flows into the inside space of the cylinder 111 on the side of the outflow-gas-supply tube part 101b, through between the check valve part 163 and the cylinder 111 and between the piston shank 123 and the cylinder 111.

At this time, the sealing members 129b and 129d continue to maintain sealing between the cylinder 111 and the piston shank 123. Further, the sealing member 129c is apart from the inner-circumferential-surface of the cylinder 111. Therefore, the gas flows into the outflow-gas-supply tube part 101b and is emitted externally from a gas/water supply nozzle.

[Switch from Gas Supply State to Water Supply State]

Next, a water supply state will be described with reference to FIG. 3D.

With the end part 125a closed by an operator's finger, the gas/water supply switch 69b is pressed by the operator's finger. The urging member 109 thereby contracts and the piston shank 123 is pressed into the cylinder 111. At this time, the piston shank 123 makes a large downward movement in relation to the cylinder 111. Further, the drop prevention part 135 separates from the bottom face 139a of the drop prevention contact part 139.

The sealing member 129d slides downward on the inner circumferential surface of the cylinder 111. The sealing part 129d is provided above the outflow-gas-supply tube part 101b and achieves sealing between the cylinder 111 and the piston shank 123.

Further, the sealing member 129c slides downward in accordance with movement of the piston shank 123. Between the outflow-gas-supply tube part 101a and the outflow-water-supply tube 101b, the sealing member 129c is in tight contact with the inner circumferential surface of the cylinder 111 and achieves sealing between the cylinder 111 and the piston shank 123.

In this manner, the inside space of the cylinder 111 on the side of the outflow-gas-supply tube part 101b is sealed by the sealing members 129c and 129d.

The sealing member 129b slides downward on the inner circumferential surface of the cylinder 111 in accordance with sliding of the piston shank 123. Further, the sealing member 129b is provided below the inflow-gas-supply tube part 101a and above the outflow-water-supply tube part 101d, and achieves sealing between the cylinder 111 and the piston shank 123.

In this manner, the inside space of the cylinder 111 on the side of the inflow-gas-supply tube part 101a is sealed by the sealing members 129b and 129c.

Further, in accordance with movement of the piston shank 123, the sealing member 129a moves downward to a lateral side of the inflow-water-supply tube part 101c and moves apart from the inner circumferential surface of the cylinder 111. Therefore, the sealing member 129a does not achieve sealing between the cylinder 111 and the piston shank 123.

Accordingly, the inflow-water-supply tube part 101c communicates with the outflow-water-supply tube part 101d through the inside space of the cylinder 111 which is provided below the sealing member 129b. Therefore, a gas is supplied to the water supply apparatus 83 through the channel part 85 from the gas supply apparatus 81. When the internal pressure of the water supply apparatus 83 increases, a liquid, filled in the water supply apparatus 83, flows into the inflow-water-supply tube part 101c. Therefore, the liquid flows from the inflow-water-supply tube part 101c to the outflow-water-supply tube part 101d through the inside space of the cylinder 111 which is provided in the lower side of the sealing member 129b. In this manner, a liquid is emitted externally from the gas/water supply nozzle.

The gas which flows from the gas supply apparatus 81 flows also into the cylinder 111 through the inflow-gas-supply tube part 101a. However, since the sealing members 129b and 129c seal the inside space of the cylinder 111 on the side of the inflow-gas-supply tube part 101a, the gas steadily flows into the water supply apparatus 83.

In the water supply state, the sealing member 129c seals the inside space of the cylinder 111 on the side of the outflow-gas-supply tube part 101b. Therefore, a gas does not flow into the inside space of the cylinder 111 on the side of the outflow-gas-supply tube part 101b. Therefore, when the channel switching apparatus 100 switches from the gas supply state shown in FIG. 3B to the water supply state shown in FIG. 3D, the gas which remains in the inside space of the cylinder 111 on the side of the outflow-gas-supply tube part 101b continues to be emitted from the side of the outflow-gas-supply tube part 101b. As a result, the pressure of the inside space on the side of the outflow-gas-supply tube part 101b drops.

When the channel switching apparatus 100 switches from the gas supply state shown in FIG. 3B to the water supply state shown in FIG. 3D, the check valve unit 160 moves in accordance with movement of the piston shank 123, with the check valve part 163 closed as shown in FIG. 3B. At this time, the check valve part 163 opens in accordance with the drop in pressure as described above. The upper end part 163b of the check valve part 163 makes tight contact with the inner circumferential surface of the cylinder 111.

Furthermore, when the channel switching apparatus 100 switches from the gas supply state shown in FIG. 3B to the water supply state shown in FIG. 3D, the check valve unit 163 moves downward with the tapering lower end part 163a oriented as a head. Therefore, the check valve part 163 moves without being turned over.

[Switch from Water Supply State to Non-Operation State]

When the operator's finger separates from the end part 125a, the gas/water supply switch 69b is released. The urging member 109 thereby expands and the piston shank 123 is pressed upward in relation to the cylinder 111 by the gas/water supply switch 69b. At this time, as shown in FIG. 3A, the piston shank 123 make a large upward movement in relation to the cylinder 111 until the drop prevention part 135 is brought into contact with the bottom face 139a of the drop prevention contact part 139.

The sealing members 129a, 129b, 129c, and 129d move upward in accordance with the movement of the piston shank 123, and are arranged at the position as described with reference to the state of non-operation shown in FIG. 3A.

Furthermore, the check valve unit 160 moves upward in accordance with movement of the piston shank 123. At this time, as described with reference to the water supply state shown in FIG. 3D, the check valve part 163 is opening and the upper end part 163b of the check valve part 163 is in contact with the inner circumferential surface of the cylinder 111. Therefore, when the check valve unit 160 moves upward, the upper end part 163*b* of the check valve part 163 slides upward on the inner circumferential surface of the cylinder 111.

[Occurrence of Curl-back 180 at Check Valve Part 163]

Figure 4A:
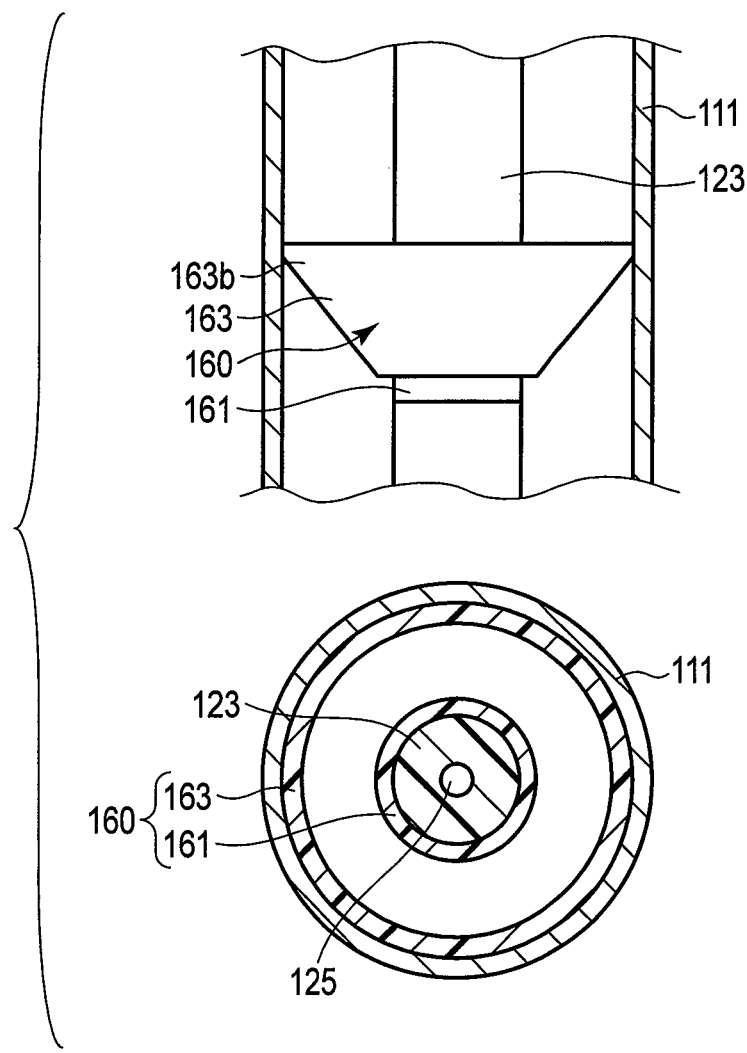
FIG. 4A shows a side view and top view of the check valve unit not provided with a low strength part or a high strength part.

Unlike the present embodiment, with reference to FIGS. 4A, 4B, and 4C, descriptions will be made of a case that the low-strength part 165 and the high-strength part 167 are not provided in the side of the upper end part 163*b* and a variation in strength does not occur. In this case, as shown in FIG. 4A, the side of the upper end part 163*b* has uniform strength in the circumferential directions of the check valve unit 160. Also in this case, as shown in FIG. 4A, neither thin parts 165*a* nor thick parts 167*a* are provided on the side of the upper end part 163*b*, and a variance in thickness does not occur. In this case, as shown in FIG. 4A, the side of the upper end part 163*b* has uniform thickness in the circumferential directions of the check valve unit 160.

As shown in FIG. 4B, when the upper end part 163*b* slides upward on the inner circumferential surface of the cylinder 111 when the strength level is uniform, a part on the side of the upper end part 163*b* is turned over by sliding resistance, and curl-back 180 occurs. This curl-back 180 causes so as to be folded from the inside part of the check valve part 163 to the outside part of the check valve part 163. The curl-back 180 spreads from the upper side to the lower side in the axial directions of the check valve part 163. The curl-back 180 as described occurs more frequently as the number of times that slide movement has taken place increases.

Figure 4C:
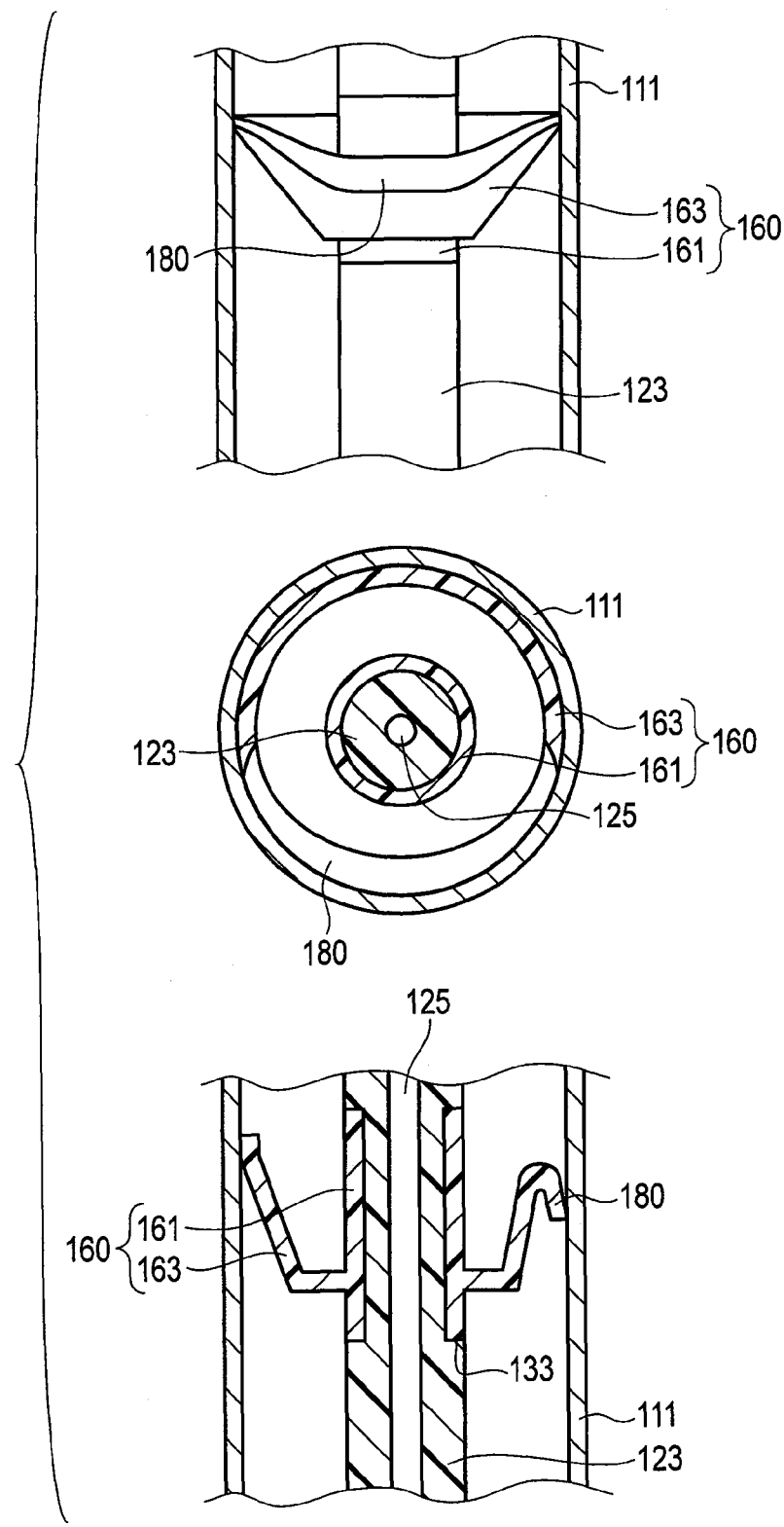
FIG. 4C shows a side view, a top view, and a cross-sectional view in a state in which curl-back has spread in directions to the periphery of the check valve part shown in FIG. 4B.

The curl-back 180 occurring at a part of the upper end part 163*b* as shown in FIG. 4B spreads in the circumferential directions of the check valve part 163, as shown in FIG. 4C, in accordance with an increase in the number of times that slide movement takes place since the strength is uniform.

Further, when the number of times slide movement takes place increases, the curl-back 180 spreads over the entire circumference of the upper end part 163*b*. As a result, the side of the upper end part 163*b* is turned over along the entire circumference.

Thus, the curl-back 180 increases as the number of times slide movement takes place increases. As a result, the check valve part 163 deforms from its initial state as shown in FIG. 4A.

Furthermore, when the side of the upper end part 163*b* is turned over along the entire circumference, the curl-back 180 cannot be corrected even if a gas flows toward the side of the check valve part 163 in the gas supply state shown in, for example, FIG. 3B. As a result, the shape of the check valve part 163 continues to deform from the initial state shown in FIG. 4A.

In this manner, the upper end part 163*b* of the check valve part 163 does not securely make tight contact with the inner circumferential surface of the cylinder 111 in the state shown in FIG. 3A, and the check valve part 163 may fail to achieve sealing between the cylinder 111 and the piston shank 123. Thus, a risk arises that the check valve part 163 will not function as a valve, and giving rise to a risk of not achieving sealing.

Therefore, the durability of the check valve part 163 drops, and thus the replacement frequency of the check valve part 163 increases.

[Prevention of Spreading of Curl-back 180]

Particularly when repeatedly switching from the water supply state shown in FIG. 3D to the non-operation state shown in FIG. 3A, the upper end part 163*b* of the check valve part 163 repeatedly slides upward on the inner circumferential surface of the cylinder 111. The outer circumferential surface of the upper end part 163*b* is thereby worn out by sliding resistance. The more the outer circumferential surface is worn out, the more easily the curl-back 180 as described above occurs.

However, as shown in FIG. 2D, according to the present embodiment, the low-strength parts 165 and the high-strength parts 167 are provided in the side of the upper end part 163*b* Therefore, the strength levels of the parts varies. In other words, in the side of the upper end part 163*b*, there is a variation in the strength levels of the check valve unit 160 in the circumferential directions due to the low-strength parts 165 and the high-strength parts 167. Also in the side of the upper end part 163*b*, the thin parts 165*a* and thick parts 167*a* are provided, and variation is therefore caused in thickness. In other words, in the side of the upper end part 163*b*, there is variation in the thickness levels of the check valve unit 160 in the circumferential directions due to the thin parts 165*a* and the thick parts 167*a*.

When the upper end part 163*b* slides upward on the inner circumferential surface of the cylinder 111, as shown in FIG. 4D, a low-strength part 165 is turned over ahead of any high-strength part 167 due to sliding resistance since, for example, the strength of the low-strength part 165 as a part on the side of the upper end part 163*b* is smaller than the strength of the high-strength part 167. That is, the low-strength parts 165 are provided to cause variation in strength of the upper end part 163*b*, and causes curl-back 180 to occur at and concentrate on the low-strength part 165 owing to the variation in strength.

The curl-back 180 occurring at the low-strength part 165 as shown in FIG. 4D acts to spread throughout the entire circumference in the side of the upper end part 163*b*, in accordance with increase in number of times slide takes place. However, in the present embodiment, the high-strength part 167 has greater strength than the low-strength part 165. Therefore, as shown in FIG. 4D, the high-strength part 167 prevents this curl-back 180 from spreading throughout the entire circumference in the side of the upper end part 163*b*. That is, as shown in FIG. 4D, the high-strength part 167 functions as a breakwater against the curl-back 180. As a result, in the side of the upper end part 163*b*, the entire circumference is prevented from being turned over.

Also, the curl-back 180 increases at the low-strength parts 165 as the number of times slide movement takes place increases. However, as shown in FIG. 4D, the high-strength parts 167 prevent the curl-back 180 from spreading throughout the entire circumference in the side of the upper end part 163*b*, without influence from the number of times slide takes place. As a result, in the side of the upper end part 163*b*, the entire circumference is prevented from being turned over.

Thus, the shape of the check valve part 163 incurs almost no deformation from the initial state shown in FIG. 3A.

Since the curl-back 180 occurs only at the low-strength parts 165, for example, a gas flows to the side of the check valve part 163 in the gas supply state shown in, for example, FIG. 3B. Therefore, curl-back at the upper end part 163*b* is cleared easily by the gas only. As a result, the shape of the check valve part 163 easily returns to the initial state.

In this manner, the check valve part 163 is in tight contact with the inner circumferential surface of the cylinder 111 in the non-operation state shown in FIG. 3A and thereby achieves sealing between the cylinder 111 and the piston shank 123. Thus, the check valve part 163 functions as a valve and achieves sealing.

Therefore, durability of the check valve part 163 improves, and frequency of replacing the check valve part 163 decreases accordingly.

As described above, when switching from the water supply state shown in FIG. 3D to the non-operation state shown in FIG. 3A is repeatedly performed, the upper end part 163b of the check valve part 163 repeatedly slides upward on the inner circumferential surface of the cylinder 111. The outer circumferential surface of the upper end part 163b is thereby worn out by sliding resistance. The more the outer circumferential surface is worn out, the more easily the curl-back 180 as described above occurs. However, as also described above, the high-strength parts 167 prevent this curl-back 180 from spreading throughout the entire circumference in the side of the upper end part 163b. As a result, in the side of the upper end part 163b, curl-back of the entire circumference is prevented.

[Cleaning of Channel Switching Apparatus 100]

Next, cleaning of the channel switching apparatus 100 will be described.

The piston 121 can be pulled from the cylinder 111 and cleaned. At this time, the outer circumferential surface, communication channel 125, and through-hole 127 of the piston shank 123 are not covered with the check valve part 163 but are steadily exposed, as shown in FIG. 2C. In this way, a cleaning liquid fully flows through these components in this manner, without being influenced by the check valve part 163.

[Advantageous Effects]

In the present embodiment, the low-strength parts 165 and the high-strength parts 167 are arranged alternately in the circumferential directions of the check valve unit 160, and have strength levels which differ from each other. The low-strength parts 165 and the high-strength parts 167 are provided in a plurality to be equal in number.

Therefore, in the present embodiment, even when curl-back 180 is caused by slide movement of the check valve part 163, the curl-back 180 can be prevented from spreading throughout the entire circumference of the upper end part 163b by the high-strength parts 167.

Also in the present embodiment, the curl-back 180 can be prevented from spreading throughout the entire circumference of the upper end part 163b by the high-strength part 167, without influence from the number of times of slide movement.

In this manner, according to the present embodiment, deformation of the shape of the check valve part 163 from deforming from the initial state can be suppressed.

Also according to the present embodiment, the curl-back 180 occurs only at the low-strength parts 165. Therefore, in the present embodiment, the curl-back 180 can be cleared easily by only a gas as the gas flows to the side of the check valve part 163, for example, in the gas supply state. As a result, the shape of the check valve part 163 can be easily returned to the original state.

Thus in the present embodiment, even if a part of the check valve part 163 is turned over when the check valve part 163 repeatedly slides on the inner circumference of the cylinder 111, the curl-back 180 can be prevented from spreading to a wide area, the durability of the check valve part 163 can be improved, and the frequency of replacing the check valve part 163 can be reduced.

Also in the present embodiment, the length L1 of each low-strength parts 165 is shorter than the length L2 of each high-strength parts 167, in the circumferential directions of the check valve unit 160. Therefore, occurrence of curl-back 180 can be prevented.

In the present embodiment, as shown in FIGS. 3B and 3C, the high-strength parts 167 are separated from the inner circumferential surface of the cylinder 111 and the low-strength parts 165 are in tight contact with the inner circumferential surface of the cylinder 111, in the gas supply state, however such condition is not necessarily limited to this.

Figure 5C:
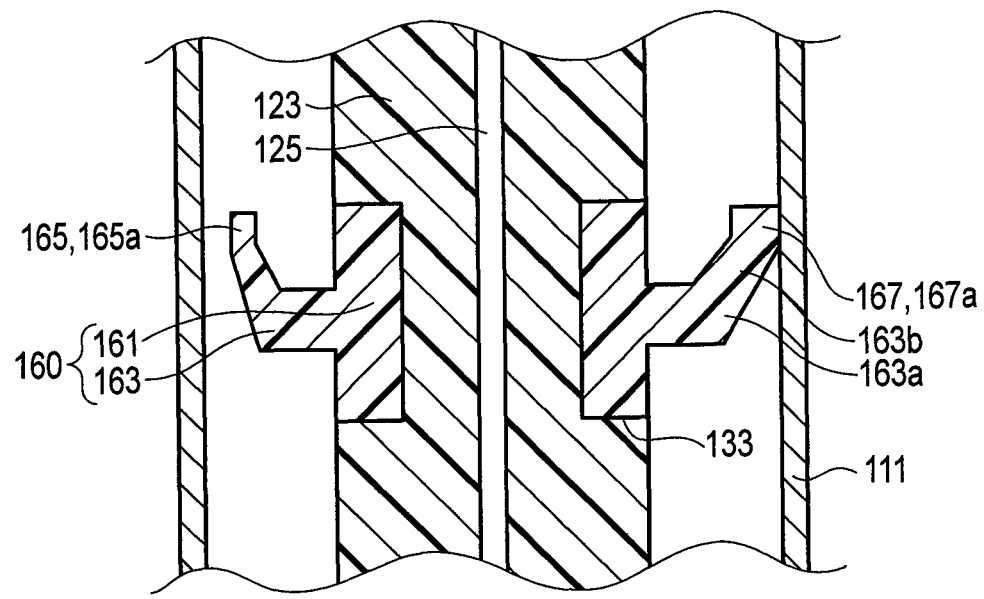
FIG. 5C shows the periphery of the check valve unit along a line 5C-5C shown in FIG. 5B.

As shown in FIG. 5A, in the circumferential directions of the check valve unit 160, for example, the length L1 of each low-strength parts 165 may be longer than the length L2 of each high-strength parts 167. In this manner, as shown in FIGS. 5B and 5C, the high-strength parts 167 make tight contact with the inner circumferential surface of the cylinder 111, and the low-strength parts 165 are separated from the cylinder 111, in the gas supply state.

Of course, in the gas supply state, both the low-strength parts 165 and the high-strength parts 167 may also close.

Thus, if the check valve part 163 can close and allow a gas to flow in the gas supply state, for example, at least either or both of the low-strength parts 165 or the high-strength parts 167 should close, for example.

[Second Embodiment]

Figure 6:
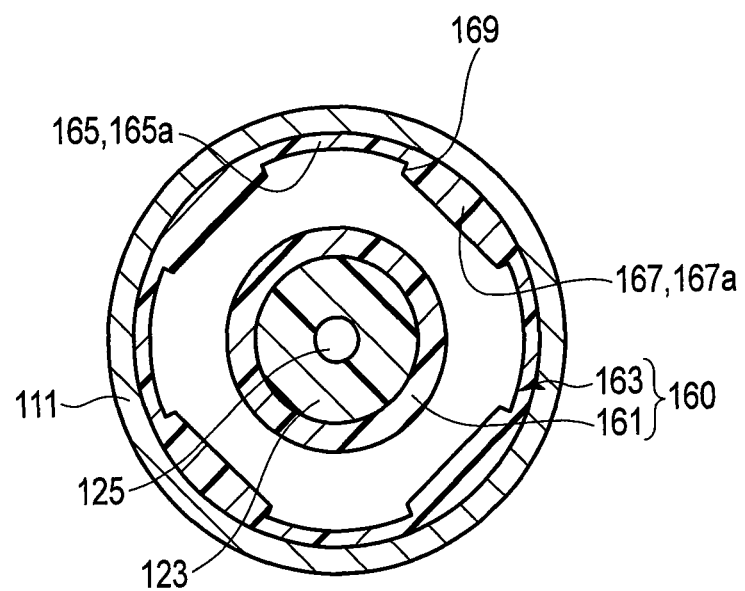
FIG. 6 is a top view of a check valve unit according to the second embodiment.

With reference to FIG. 6, the second embodiment will be described. The present embodiment will be described hereinafter with respect only to configurations different from the first embodiment.

[Configuration]

[Low-Strength Parts 165 and High-Strength Parts 167]

In the present embodiment, low-strength parts 165 and high-strength parts 167 are continuous in the circumferential directions of the check valve unit 160 in a manner that a step part 169 is formed between the low-strength parts 165 and the high-strength parts 167 in the circumferential directions of the check valve unit 160.

[Advantageous Effects]

In the present embodiment, since the step part 169 is formed, a load applied to the high-strength parts 167 from the low-strength parts 165 can be reduced when the low-strength parts 165 are turned over. In this manner, according to the present embodiment, curl-back 180 can be more securely prevented from spreading to the high-strength parts 167 from the low-strength parts 165, and the high-strength parts 167 can be prevented from being turned over.

[Third Embodiment]

With reference to FIGS. 7A and 7B, the third embodiment will be described. The present embodiment will be described hereinafter with respect only to configurations different from the first embodiment.

[Configuration]

[Reinforcement Part 171]

The check valve unit 160 further comprises a reinforcement part 171 which is provided in a side closer to a lower end part 163a of a check valve part 163 than an upper end part 163b thereof, on a circumferential surface of the check valve part 163, suppresses curl-back of the check valve part 163 and increases the thickness of the check valve part 163. The reinforcement part 171 is preferably provided at a root section of the low-strength parts 165.

The reinforcement part 171 suppresses an increase of the amount of curl-back of the low-strength parts 165 in axial directions of the check valve part 163 when the low-strength parts 165 are turned over. The reinforcement parts 171 suppresses, for example, the low-strength parts 165 from being turned over from the side of the upper end part 163b to the side of the lower-end-part 163a.

[Advantageous Effects]

In the present embodiment, the amount of curl-back of the low-strength parts 165 can be suppressed by the reinforcement part 171, and deformation of the check valve part 163 can be suppressed. As a result, according to the present embodiment, the durability of the check valve part 163 can further be improved, and the frequency of replacing the check valve part 163 can also further be decreased.

The present invention is not limited directly to the embodiment but, in practical phases, may be practiced with components modified within a scope not deviating from the subject matters of the invention. Various inventions can further be made by appropriately combining a plurality of components disclosed in the embodiments described above.

What is claimed is:

1. An endoscope channel switching apparatus which comprises a cylinder connected to a plurality of channel parts, and a piston detachably fitted into the cylinder, the apparatus switching communication states of the channel parts in accordance with movement of the piston in relation to the cylinder, and the apparatus comprising:
   a check valve unit which is provided on the piston and which moves together with the piston in accordance with movement of the piston in relation to the cylinder, wherein:
   the check valve unit comprises a low-strength part and a high-strength part which are provided at a side of an upper part of the check valve unit, and which are arranged alternately in a circumferential direction of the check valve unit, and which have strength levels different from each other,
   the check valve unit opens and closes in accordance with an internal pressure inside the cylinder,
   when the check valve unit closes, at least a part of the check valve unit separates from an inner circumferential surface of the cylinder,
   when the check valve unit opens, the check valve unit makes tight contact with the inner circumferential surface of the cylinder throughout an entire circumference thereof, thereby achieving sealing between the cylinder and the piston, and
   when the check valve unit moves together with the piston, the check valve unit slides on the inner circumferential surface of the cylinder.

2. The endoscope channel switching apparatus according to claim 1, wherein:
   the low-strength part comprises a thin part of the check valve unit, and
   the high-strength part comprises a thick part of the check valve unit.

3. The endoscope channel switching apparatus according to claim 1, wherein the low-strength part separates from the inner circumferential surface of the cylinder during supply of a gas.

4. The endoscope channel switching apparatus according to claim 1, wherein the low-strength part and the high-strength part each are provided in a plurality and equal in number.

\* \* \* \* \*